(12) United States Patent
Ma et al.

(10) Patent No.: US 10,471,154 B2
(45) Date of Patent: Nov. 12, 2019

(54) SPIROCYCLIC INDOLONE POLYETHYLENE GLYCOL CARBONATE COMPOUND, COMPOSITION, PREPARATION METHOD AND USE THEREOF

(71) Applicant: Fei Xiao, Beijing (CN)

(72) Inventors: Jie Ma, Beijing (CN); Fei Xiao, Beijing (CN); Hongjun Ren, Beijing (CN); Wei Wang, Beijing (CN); Hongtao Xu, Beijing (CN); Meng Wang, Beijing (CN); Lihui Zou, Beijing (CN); Fei Ding, Beijing (CN); Fei Su, Beijing (CN)

(73) Assignee: Fei Xiao, Beijing (CN)

( * ) Notice: Subject to any disclaimer, the term of this patent is extended or adjusted under 35 U.S.C. 154(b) by 0 days.

(21) Appl. No.: 16/324,034

(22) PCT Filed: Aug. 8, 2016

(86) PCT No.: PCT/CN2016/093954
§ 371 (c)(1),
(2) Date: Feb. 7, 2019

(87) PCT Pub. No.: WO2018/027477
PCT Pub. Date: Feb. 15, 2018

(65) Prior Publication Data
US 2019/0209700 A1    Jul. 11, 2019

(51) Int. Cl.
*C07D 487/10*    (2006.01)
*A61K 47/60*    (2017.01)
*A61K 31/407*    (2006.01)
*A61P 35/00*    (2006.01)

(52) U.S. Cl.
CPC ............ *A61K 47/60* (2017.08); *A61K 31/407* (2013.01); *A61P 35/00* (2018.01); *C07D 487/10* (2013.01)

(58) Field of Classification Search
CPC .................................................. C07D 487/10
See application file for complete search history.

(56) References Cited

U.S. PATENT DOCUMENTS

2012/0071499 A1    3/2012  Chu et al.

FOREIGN PATENT DOCUMENTS

WO    2011134925 A1    11/2011
WO    2016028391 A2    2/2016

*Primary Examiner* — Laura L Stockton
(74) *Attorney, Agent, or Firm* — Weisun Rao; Jun Chen; Venture Partner, LLC

(57) ABSTRACT

The present invention relates to a spirocyclic indolone polyethylene glycol carbonate compound, a composition thereof, a preparation method therefor, and a use thereof as an anticancer drug due to the antitumor activity thereof. The structural formula of the spirocyclic indolone polyethylene glycol carbonate compound is shown below. The compound has excellent tumor inhibitory activity, water solubility, low toxicity, and can be used for intravenous injection.

11 Claims, 9 Drawing Sheets

Fig.1

SPIROCYCLIC INDOLONE POLYETHYLENE GLYCOL CARBONATE COMPOUND, COMPOSITION, PREPARATION METHOD AND USE THEREOF

TECHNICAL FIELD

The present invention pertains to the field of medicine, and relates to spirocyclic indolone polyethylene glycol carbonate compounds, and compositions thereof, to processes for their preparation, and to the use thereof as anticancer drugs due to their antitumor activity.

BACKGROUND

Cancer threatens human health and life. In recent years, researches on anticancer drugs have turned to the development of specific molecular targeted therapeutic drugs.

The p53 tumor suppresser protein plays a critical role in protection against development of tumor. In about 50% of human cancers the gene encoding the p53 protein occur mutation or deletion, resulting in loss of the transcriptional activity and the functions of the tumor suppressor protein. In the remaining 50% cases, direct interaction between p53 and human murine double minute 2 (MDM2) proteins plays a major role in inhibiting the functions of wild-type p53. Intervention of the interaction between MDM2-p53 with a small molecule has been considered as a new strategy for cancer treatment.

Since 2005, Wang Shaomeng et al. have reported a series of spiro-indolone analogs as inhibitors of MDM2-p53 interaction, and one (SAR405838/MI-77301) among this series of compounds has currently been in clinical development (see U.S. Pat. No. 7,759,383B2, U.S. Pat. No. 8,222,288B2, U.S. Pat. No. 8,680,132B2, US20130030173A1, WO2012065022A2, and WO2012155066A2). Swiss Roche Pharmaceuticals also reports a series of spiro-indolone analogs (see WO2011067185, WO2011134925, and WO2012022707) and a series of pyrrolidine analogs (see WO2013178570, WO2014206866, and WO2015000945), wherein RG7388 among the pyrrolidine analogs has been in clinical development. It has been shown that these compounds have limited solubility, greatly challenging the development of preparations which are stable in vivo and in clinical researches.

The existing compounds can only be used in oral preparations due to poor water solubility, and have compromised therapeutic effect against tumors in clinical due to severe gastrointestinal effects and low bioavailability. Accordingly, there is still a need for developing spiro-indolone analogs that have excellent solubility in water, low toxicity, and more potency and can be used in dosage forms for intravenous injection, as inhibitors of the MDM2-p53 interaction.

SUMMARY OF THE INVENTION

Technical Problem

Therefore, an object of the present disclosure is to provide a spirocyclic indolone polyethylene glycol carbonate compound which has excellent solubility in water, low toxicity, and more potency and can be used in dosage forms for intravenous injection, or a stereoisomer thereof, or a pharmaceutically acceptable salt thereof;

Another object of the present disclosure is to provide a process for preparing the above-mentioned spirocyclic indolone polyethylene glycol carbonate compound;

Still another object of the present disclosure is to provide an antitumor pharmaceutical composition;

Still yet another object of the present disclosure is to provide use of the above-mentioned spirocyclic indolone polyethylene glycol carbonate compound, a stereoisomer thereof, or a pharmaceutically acceptable salt thereof, in the manufacture of a medicament for treating cancer;

It is still another object of the present disclosure to provide a method of treating cancer.

Technical Solutions

In an aspect, the present disclosure provides a spirocyclic indolone polyethylene glycol carbonate compound represented by the following general formula I, a stereoisomer thereof, or a pharmaceutically acceptable salt thereof:

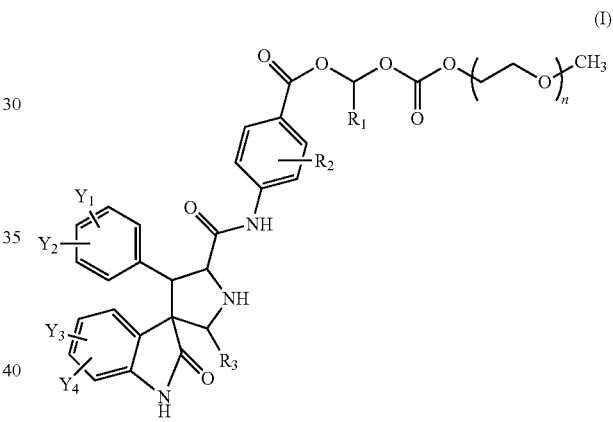

in the general formula I:

$Y_1$, $Y_2$, $Y_3$, and $Y_4$ are each independently selected from the group consisting of H and halogen;

$R_1$ is selected from the group consisting of H and C1-C5 alkyl;

$R_2$ is selected from the group consisting of H, C1-C5 alkyl and C1-C5 alkoxy;

$R_3$ is selected from the group consisting of C1-C10 alkyl and C2-C10 alkenyl; and n is an integer of 1 to 80.

In another aspect, the present disclosure provides a process for preparing the above-mentioned spirocyclic indolone polyethylene glycol carbonate compound, comprising: subjecting a spirocyclic indolone compound represented by the following general formula III with a compound represented by the following general IV to a nucleophilic substitution reaction in the presence of a base to provide said spirocyclic indolone polyethylene glycol carbonate compound,

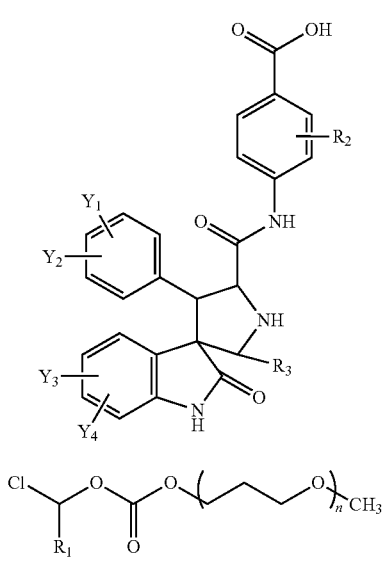

wherein, $Y_1$, $Y_2$, $Y_3$, $Y_4$, $R_1$, $R_2$, $R_3$, and n are as defined above.

In still another aspect, the present disclosure provides an antitumor pharmaceutical composition comprising a therapeutically effective amount of a spirocyclic indolone polyethylene glycol carbonate compound represented by the above general formula I, a stereoisomer thereof, or a pharmaceutically acceptable salt, and one or more pharmaceutically acceptable auxiliary materials.

In still yet another aspect, the present disclosure provides use of a spirocyclic indolone polyethylene glycol compound represented by the general formula I, a stereoisomer thereof, or a pharmaceutically acceptable salt thereof, in the manufacture of a medicament for treating cancer.

In still another aspect, the present disclosure provides a method for treating cancer, comprising administering to a cancer patient a therapeutically effective amount of a spirocyclic indolone polyethylene glycol carbonate compound represented by the general formula I, a stereoisomer thereof, or a pharmaceutically acceptable salt thereof.

Technical Effects

The spirocyclic indolone polyethylene glycol carbonate compounds of the present disclosure, stereoisomers thereof or pharmaceutically acceptable salts thereof, have excellent tumor suppressing activity, good solubility in water, low toxicity, and can be prepared into dosage forms for intravenous injection.

DESCRIPTION OF THE DRAWINGS

FIG. 1 is a $^1$H NMR spectrum of the compound prepared in Example 6;

DETAILED DESCRIPTION OF THE INVENTION

Figure 2:
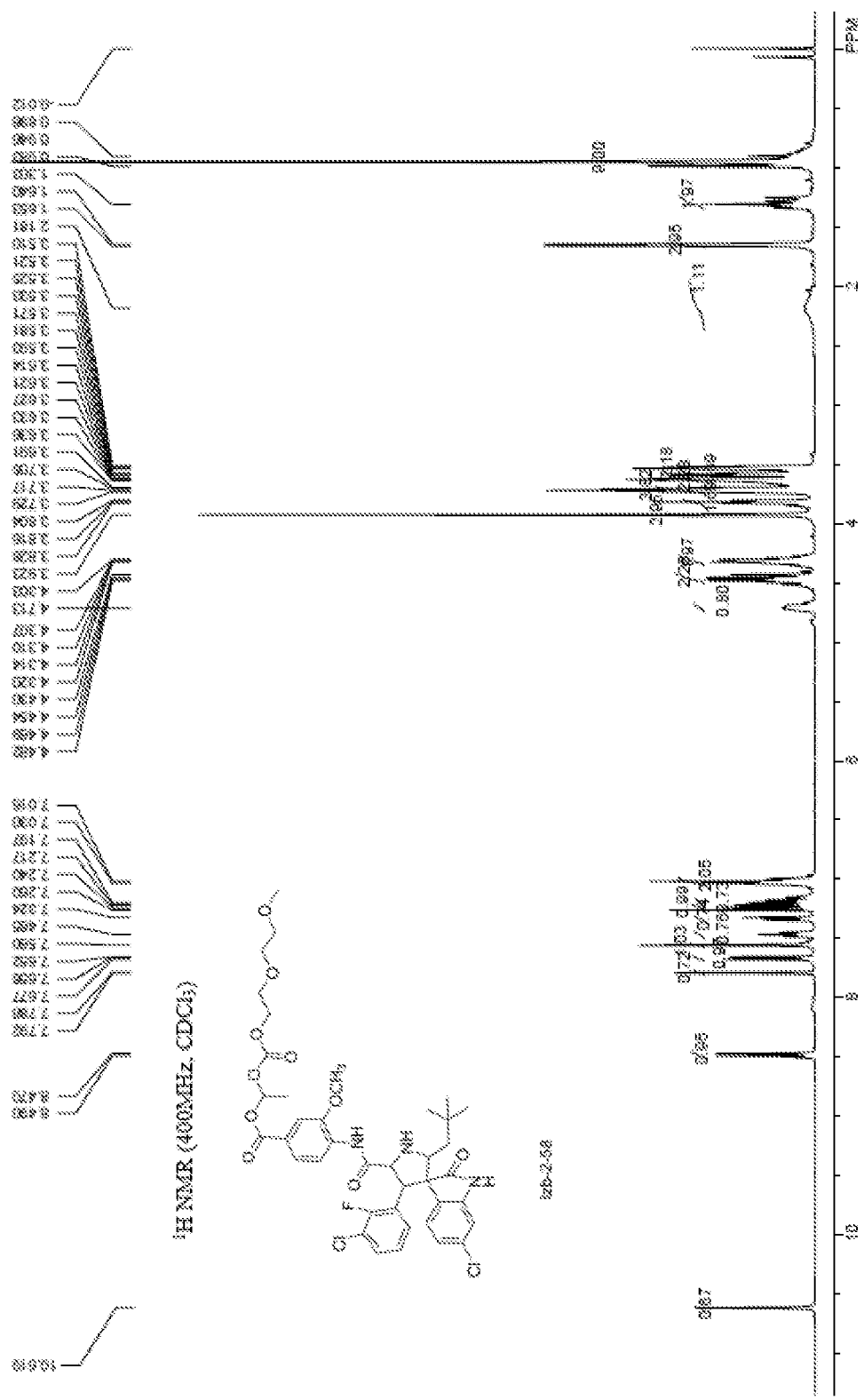
FIG. 2 is a $^1$H NMR spectrum of the compound of the invention prepared in Example 8.

Hereinafter, the present disclosure will be specifically described.

Among the spirocyclic indolone polyethylene glycol carbonate compounds according to the present disclosure, stereoisomers thereof or pharmaceutically acceptable salts thereof, in a preferred embodiment, the spirocyclic indolone polyethylene glycol carbonate compounds are preferably spirocyclic indolone polyethylene glycol carbonate compounds represented by the following formula II:

wherein, $Y_1$, $Y_2$, $Y_3$, $Y_4$, $R_1$, $R_2$, and n are as defined above.

In further preferred embodiments, $Y_1$, $Y_2$, $Y_3$, and $Y_4$ are preferably each independently selected from the group consisting of H, F and Cl;

$R_1$ is preferably selected from the group consisting of H and C1-C3 alkyl, and $R_1$ is more preferably methyl or ethyl, and most preferably methyl;

R₂ is preferably selected from the group consisting of C1-O5 alkoxy groups, and R₂ is more preferably methoxy or ethoxy, and most preferably methoxy;

R₃ is preferably selected from the group consisting of C1-C6 alkyl groups, and R₃ is more preferably pentyl, and most preferably neopentyl; n is preferably an integer of 1 to 60, more preferably an integer of 2 to 50, and most preferably an integer of 3 to 50.

The spirocyclic indolone polyethylene glycol carbonate compounds represented by the general formula I according to the present disclosure may exhibit tautomerism or structural isomerism. This indicates that the invention encompasses any tautomeric or structural isomeric forms of these compounds, or mixtures of such forms, and is not limited to any one tautomeric or structural isomeric form depicted in the structural formulas above.

Pharmaceutically acceptable salts of the spirocyclic indolone polyethylene glycol carbonate compounds according to the present disclosure refers to conventional acid-addition salts that are formed by reaction of the compounds with suitable non-toxic organic acids, such as p-toluene sulfonic acid, salicylic acid, oxalic acid, citric acid, lactic acid, malic acid, and the like, or inorganic acids, such as hydrochloric acid, sulfuric acid, phosphoric acid, nitric acid, and the like; or conventional base-addition salts formed by reaction of the compounds with suitable non-toxic organic or inorganic bases; examples of the base-addition salts include ammonium salts, sodium salts, potassium salts, and quaternary ammonium hydroxides.

The process for preparing the spirocyclic indolone polyethylene glycol carbonate compound provided by the present disclosure comprises: reacting a spirocyclic indolone compound represented by the following formula III with a compound represented by the following formula IV by a nucleophilic substitution reaction in the presence of a base to give said spirocyclic indolone polyethylene glycol carbonate compound

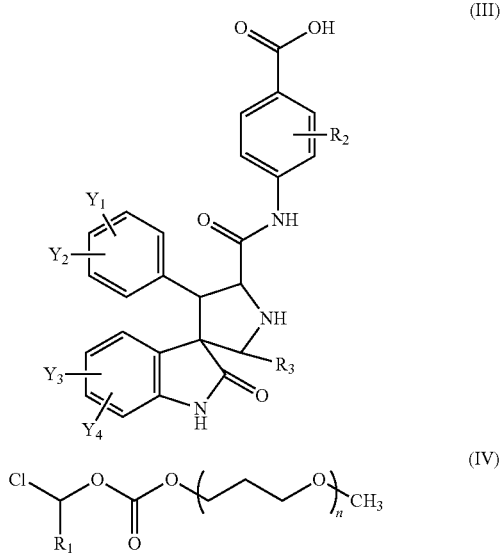

wherein Y₁, Y₂, Y₃, Y₄, R₁, R₂, R₃ and n are as defined above.

The spirocyclic indolone compounds represented by the general formula III may be prepared by the processes as described in WO2011/067185A1 and WO2011/134925A1.

The compounds represented by the general formula IV may, for example, be prepared by the reaction as follows:

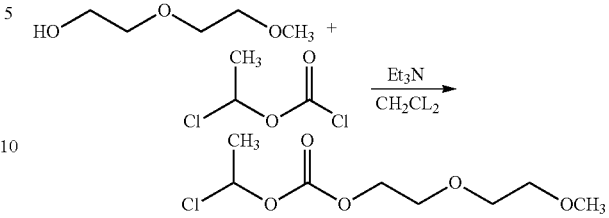

The antitumor pharmaceutical compositions provided by the present disclosure comprise a therapeutically effective amount of a spirocyclic indolone polyethylene glycol carbonate compound represented by the above general formula I, a stereoisomer thereof or a pharmaceutically acceptable salt thereof, and pharmaceutically acceptable auxiliary material(s).

The antitumor pharmaceutical compositions of the present disclosure may be formulated into injection solutions, tablets, capsules, and other dosage forms, as needed. The pharmaceutically acceptable auxiliary materials may be appropriately selected from conventional auxiliary materials depending on the dosage form to be prepared from the antitumor pharmaceutical composition. For example, when it is desirable to prepare into a lyophilized product for injection, the pharmaceutically acceptable auxiliary materials may include excipients, diluents, and the like.

According to the present disclosure, there is provided use of a spirocyclic indolone polyethylene glycol carbonate compound represented by the general formula I, a stereoisomer thereof or a pharmaceutically acceptable salt thereof in the manufacture of a medicament for treating cancer.

According to the present disclosure, there is provided a method for treating cancer, which comprises administering to a cancer patient a therapeutically effective amount of a spirocyclic indolone polyethylene glycol carbonate compound represented by the general formula I, a stereoisomer thereof or a pharmaceutically acceptable salt thereof.

The cancer includes, but is not limited to, bladder cancer, breast cancer, colon cancer, rectal cancer, renal cancer, liver cancer, small cell lung cancer, non-small cell lung cancer, esophageal cancer, gallbladder cancer, ovarian cancer, pancreatic cancer, gastric cancer, cervical cancer, thyroid cancer, prostate cancer, skin cancer, acute lymphocytic leukemia, chronic myeloid leukemia, acute lymphoblastic leukemia, B-cell lymphoma, T-cell lymphoma, Hodgkin's lymphoma, non-Hodgkin's lymphoma, hairy cell lymphoma, Burkett's lymphoma, acute myeloid leukemia, melanoma, endometrial cancer, head and neck cancer, glioblastoma or osteosarcoma.

The compounds of the present disclosure may be administered by any of conventional and convenient routes, including oral administration, intravenous injection, and topical injection. A therapeutically effective amount of a compound in accordance with the present invention means an amount of the compound that is effective to prevent, alleviate or ameliorate symptoms of disease or prolong the survival of a patient.

The therapeutically effective amount or dosage of a compound according to the present invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighting approximately 70 kg, a daily dose of about 10 mg to about 10,000 mg, and preferably from about 200 mg to about 1,000 mg, should be appropriate, although the upper limit may be exceeded when indicated. The daily dosage can be administered as a single dose or in divided doses, or for parenteral administration; and the daily dosage may be given as continuous infusion.

The present invention will be specifically described below by way of examples, but the scope of the present invention is not limited to these examples.

Example 1

Synthesis of Intermediate 4-amino-3-methoxybenzoic acid methyl ester

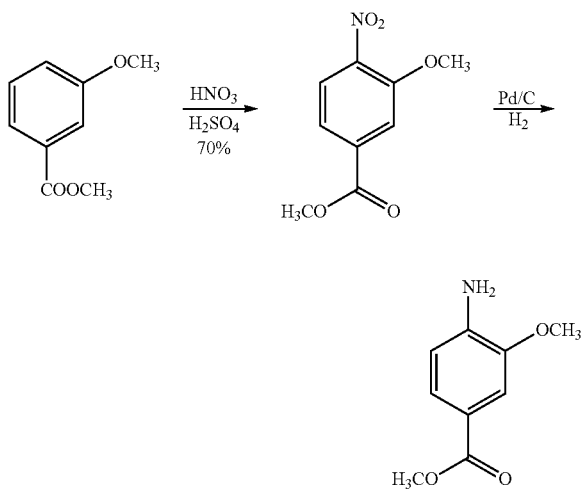

To a solution of methyl 3-methoxybenzoate (83.0 g, 500 mmol) in $H_2SO_4$ (70 wt %, 200 ml) was added $HNO_3$ (65 wt %, 40 ml) dropwise at 0° C. The resulting mixture was stirred overnight, and then poured into ice water. The mixture thus obtained was filtered, and the solid cake obtained was washed with water (3×300 ml) to give 84.4 g of 4-nitro-3-methoxybenzoic acid methyl ester as a yellow solid. Yield: 80%.

A solution of 4-nitro-3-methoxybenzoic acid methyl ester (84.4 g, 400 mmol) in ethanol (1500 ml) was stirred in the presence of Pd/carbon catalyst (10% Pd, 5.35 g) under a $H_2$ atmosphere for 5 hours. The reaction solution was then filtered through Celite® diatomite to remove the catalyst. The solvent was evaporated in vacuo to give an off white solid, which was recrystallized from methanol, giving 4-amino-3-methoxybenzoic acid methyl ester (70.95 g, 392 mmol). Yield: 98%.

$^1$H NMR (400 MHz, $CDCl_3$): δ 7.55 (dd, J=8.2 Hz, 1.4 Hz, 1H), 7.45 (d, J=8.0 Hz, 1H), 6.65 (d, J=8.0 Hz, 1H), 4.22 (s, 2H), 3.90 (s, 3H), 3.86 (s, 3H);

MS: Calcd for $C_9H_{12}NO_3$ ([M+H]$^-$): 182, found: 182.

Example 2

Synthesis of Intermediate 4-(2-((tert-butoxycarbonyl)amino)acetamido)-3-methoxybenzoic acid methyl ester

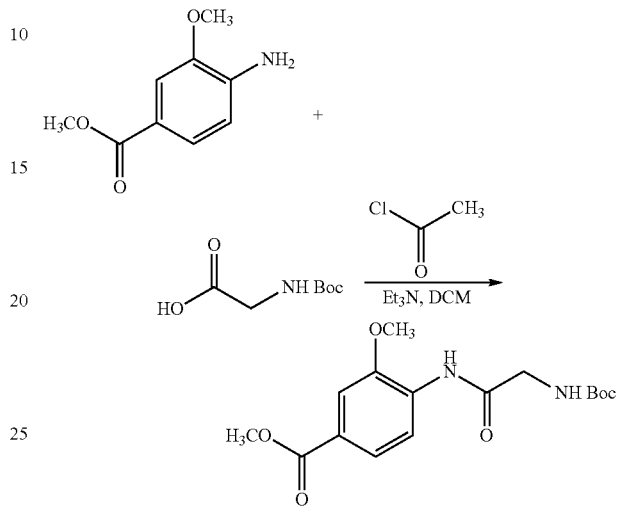

A solution of 2-((tert-butoxycarbonyl)amino)acetic acid (8.75 g, 50 mmol), $Et_3N$ (60 mmol) in dichloromethane (DCM) (150 ml) and acetyl chloride (60 mmol) was stirred under a $N_2$ atmosphere at room temperature for 1 hour. Then a solution of 4-amino-3-methoxybenzoic acid methyl ester (9.05 g, 50 mmol) in ethanol (100 ml) was added thereto. The resulting mixture was stirred overnight. Then, 200 ml of water was added to the reaction solution, and the reaction mixture was extracted with DCM (2×150 ml). The organic layers were combined, washed with water, and dried over $Na_2SO_4$ and then removed the solvents in vacuo. The residue obtained was purified by silica gel column chromatography to give 12.0 g of the target compound as a white solid. Yield: 70%.

$^1$H NMR (400 MHz, $CDCl_3$): δ 8.59 (s, 1H), 8.42 (d, J=8.4 Hz, 1H), 7.66 (d, J=8.4 Hz, 1H), 7.52 (s, 1H), 5.30 (s, 1H), 3.96 (d, J=5.2 Hz, 2H), 3.91 (s, 3H), 3.89 (s, 3H), 1.48 (s, 9H);

MS: Calcd for $C_{16}H_{23}N_2O_6$ ([M+H]$^+$): 339, found: 339.2.

Example 3

Synthesis of Intermediate 4-(2-aminoacetamido)-3-methoxybenzoic acid methyl ester hydrochloride

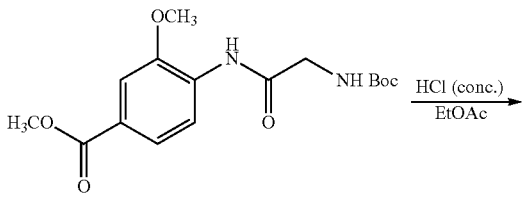

-continued

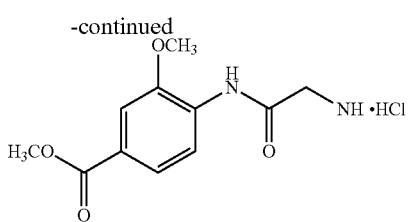

A solution of 4-(2-((tert-butoxycarbonyl)amino)acetamido)-3-methoxy benzoic acid methyl ester (11.83 g, 35 mmol) and concentrated hydrochloric acid (7.0 ml) in ethyl acetate (100 ml) was stirred overnight at room temperature. The reaction solution was then filtered, and the obtained filter cake was washed with ethyl acetate (2×50 ml), and then dried to give 6.562 g 4-(2-aminoacetamido)-3-methoxybenzoic acid methyl ester hydrochloride as a white solid. Yield: 69%.

$^1$H NMR (400 MHz, DMSO): δ 10.03 (s, 1H), 8.49 (s, 3H), 8.20 (d, J=8.4 Hz, 1H), 7.57 (d, J=8.4 Hz, 1H), 7.51 (d, J=1.2 Hz, 1H), 3.90 (s, 5H), 3.83 (s, 3H);

MS: Calcd for $C_{11}H_{15}N_2O_4$ ([M−HCl+H]$^+$): 239, found: 239.

Example 4

Synthesis of Intermediate (E)-4-(2-((3,3-dimethylbutylidene)amino)acetamido)-3-methoxybenzoic acid methyl ester

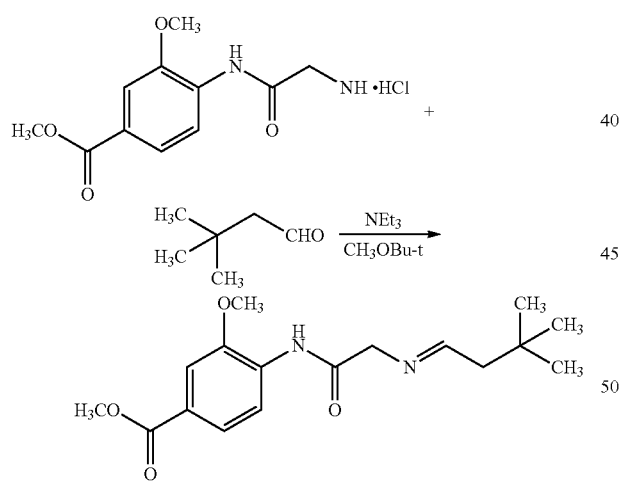

To a suspension of 4-(2-aminoacetamido)-3-methoxybenzoic acid methyl ester hydrochloride (6.56 g, 24 mmol) in MTBE (methyl t-butyl ether) (100 mL) was added triethylamine (5 ml) at room temperature. After stirring for 1 hour, 3,3-dimethyl-n-butanal (2.64 g, 26.4 mmol) was added dropwise, and the resulting mixture was stirred at room temperature for 10 hours. Then, the reaction mixture was filtered to remove triethylamine hydrochloride, and the solid cake was washed with MTBE (3×30 ml). The combined organic phases were evaporated in vacuo to remove the organic solvents, yielding a viscous oil, which was directly used for the next step without purification.

Example 5

Synthesis of Intermediate (E)-6-chloro-3-(3-chloro-2-fluorobenzylidene)indolin-2-one

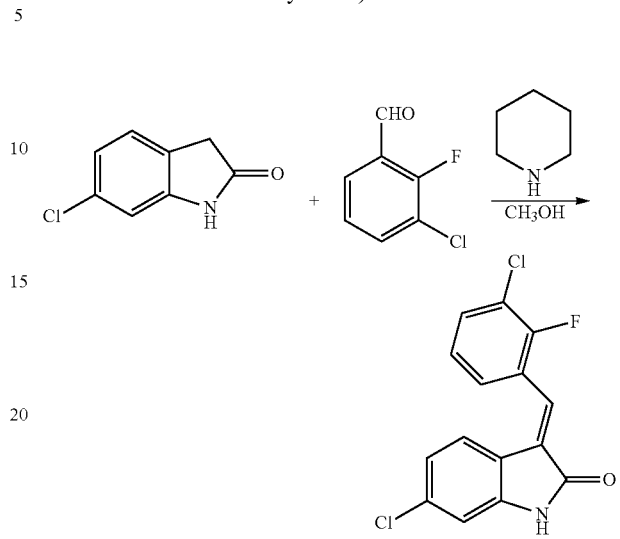

6-Chloroindolin-2-one (8.35 g, 50 mmol) and 3-chloro-2-fluorobenzaldehyde (8.295 g, 52.5 mmol) were stirred at reflux in the presence of piperidine (1 ml) for 6 hours. The reaction suspension was then filtered, and the solid obtained was washed with methanol and dried to give a yellow solid product, (E)-6-chloro-3-(3-chloro-2-fluorobenzylidene)indol-2-one (14.63 g, 47.5 mmol). Yield: 95%.

$^1$H NMR (400 MHz, DMSO): δ 10.85 (s, 1H), 7.70 (q, J=7.3 Hz 2H), 7.54 (s, 1H), 7.36 (t, J=8 Hz 1H), 7.16 (d, J=8 Hz 1H), 6.92-6.86 (m, 2H);

MS: Calcd for $C_{15}H_9Cl_2FNO$ ([M+H]$^+$): 308, found: 308.0.

Example 6

Synthesis of Intermediate rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid methyl ester

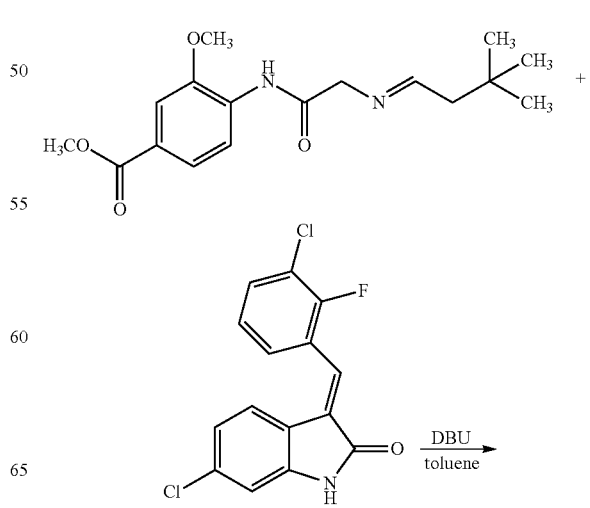

11
-continued

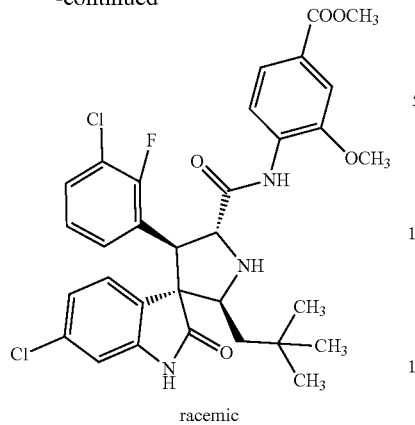

racemic

A solution of (E)-4-(2-((3,3-dimethylbutylidene)amino)acetamido)-3-methoxybenzoic acid methyl ester (24 mmol) and (E)-6-chloro-3-(3-chloro-2-fluorobenzylidene)indolin-2-one (24 mmol) in 60 ml of toluene was stirred in the presence of 1,8-diazabicycloundec-7-ene (7 ml) overnight, then 100 ml of water was added. The resulting mixture was extracted with ethyl acetate (2×150 ml). The organic layers were combined, washed with water, dried over $Na_2SO_4$, and removed the solvents in vacuo. The residue obtained was purified by silica gel column chromatography to yield 13.9 g of the target compound as a white solid. Yield: 92%.

Figure 1:
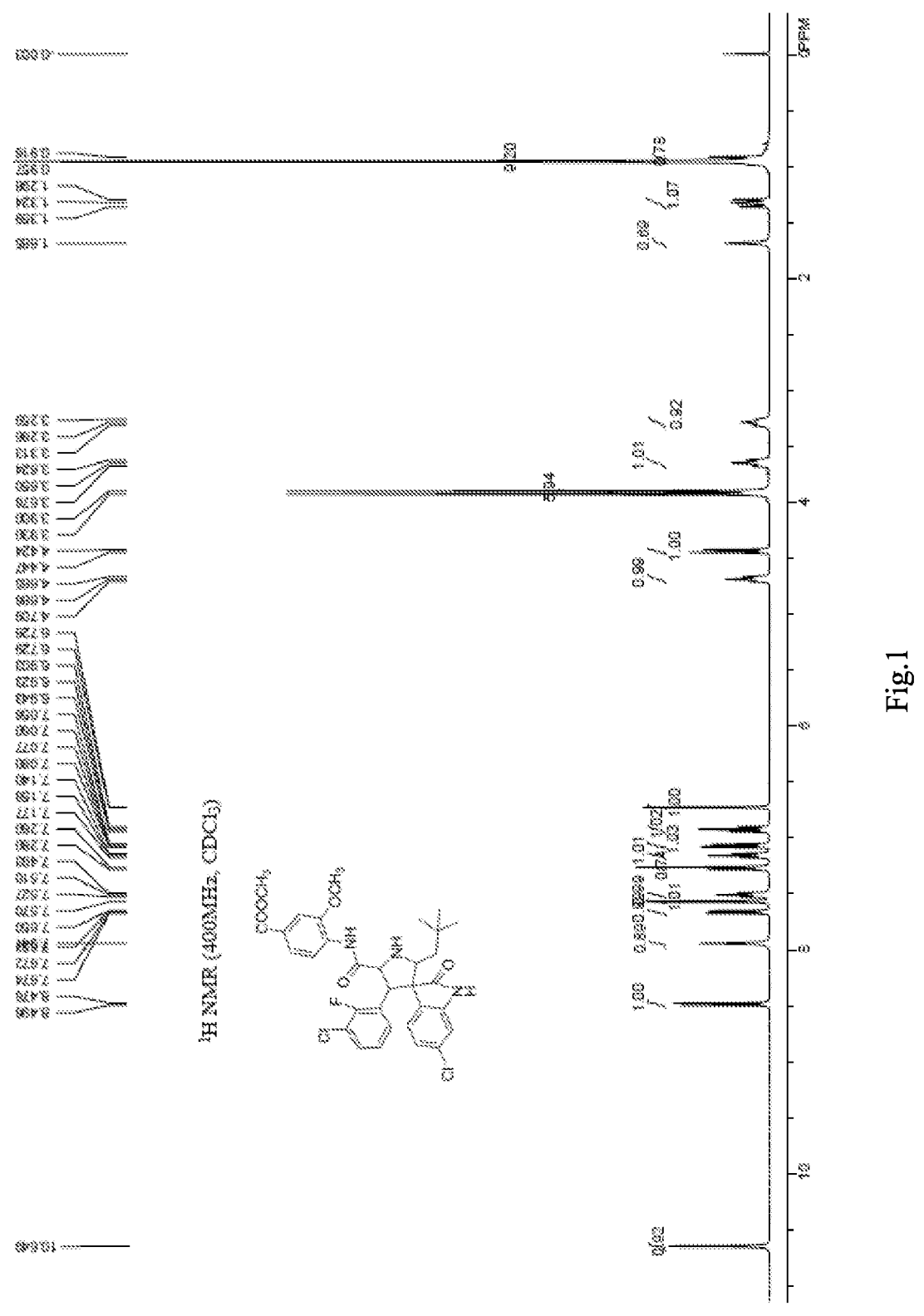

$^1$H NMR (400 MHz, $CDCl_3$): δ 10.65 (s, 1H), 8.49 (d, J=8 Hz 1H), 7.94 (s, 1H), 7.66 (dd, J=8.6 Hz J=1 Hz 1H), 7.57 (s, 1H), 7.51 (t, J=6.8 Hz 1H), 7.28 (s, 1H), 7.16 (t, J=7.4 Hz 1H), 7.07 (dd, J=8.2 Hz J=1.4 Hz 1H), 6.92 (t, J=8 Hz 1H), 6.73 (d, J=1.2 Hz 1H), 4.69 (t, J=8.8 Hz 1H), 4.44 (d, J=9.2 Hz 1H), 3.93 (s, 3H), 3.90 (s, 3H), 3.65 (t, J=10.4 Hz 1H), 3.29 (t, J=10.8 Hz 1H), 1.38-1.28 (m, 1H), 0.96 (s, 9H), 0.92 (s, 1H) (see FIG. 1);

MS: Calcd for $C_{32}H_{33}Cl_2FN_3O_5$ ([M+H]$^+$): 628, found: 628.2.

12

Example 7

Synthesis of Intermediate 1-chloroethyl (2-(2-methoxyethoxy)ethyl)carbonate

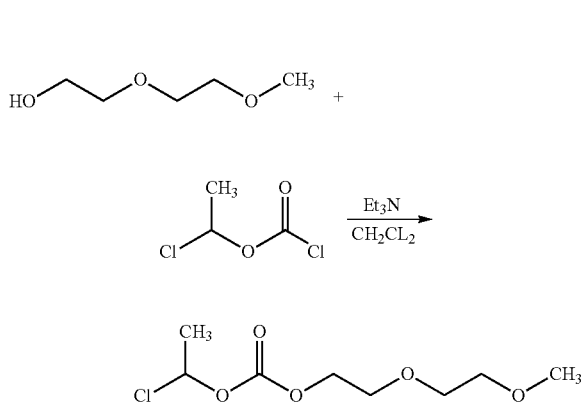

A solution of 2-(2-methoxyethoxy)ethanol (6.0 g, 50 mmol) and 1-chloroethyl chloroformate (1-chloroethyl carbonochloridate) (7.455 g, 52.5 mmol) in the presence of $Et_3N$ (4.04 g, 52.5 mmol) was stirred at room temperature for 6 hours; then, 200 ml of water was added thereto. The reaction mixture was extracted with DCM (2×150 ml). The organic layers were combined, washed with water and dried over $Na_2SO_4$. The solvents were removed in vacuo. The residue obtained was purified by silica gel column chromatography to yield 8.475 g of the target compound as an oil. Yield: 75%.

$^1$H NMR (400 MHz, $CDCl_3$): δ 6.41 (q, J=5.7 Hz 1H), 4.37-4.32 (m, 2H), 3.73 (t, J=4.8 Hz, 2H), 3.66-3.62 (m, 2H), 3.56-3.52 (m, 2H), 3.37 (s, 3H), 1.81 (d, J=6.4 Hz, 3H).

Example 8

Synthesis of Rac-9-oxo-2,5,8,10-tetraoxadodecan-11-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate (rac-SIP-PEG-2)

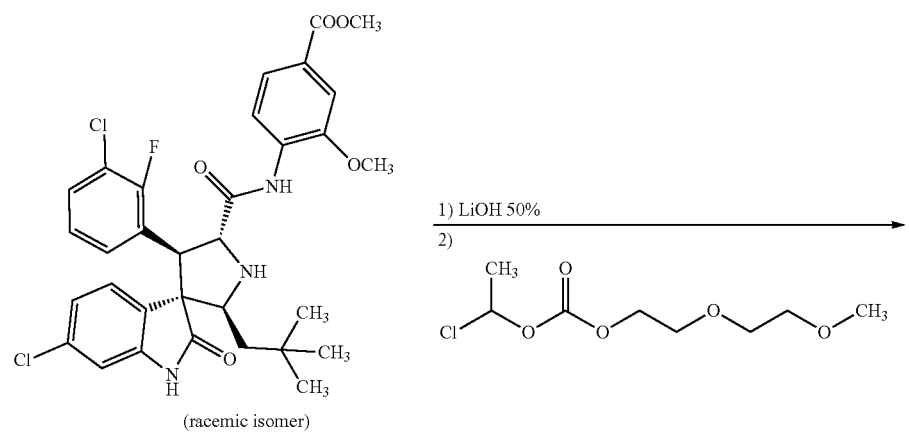

(racemic isomer)

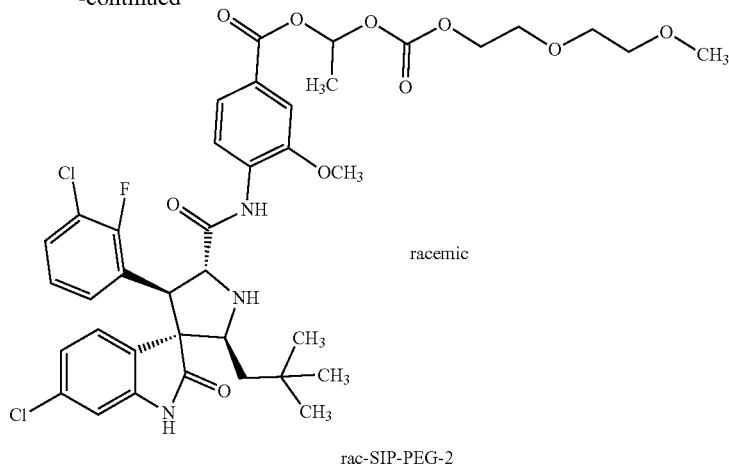

rac-SIP-PEG-2

A solution of rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid methyl ester (13.816 g, 22 mmol) in THF (20 mL) was added LiOH (5.8 ml, 50% in H₂O) and stirred overnight. After this, the reaction solution was acidified with hydrochloric acid to pH=1, and the obtained reaction mixture was extracted with ethyl acetate (3×50 ml). The organic layers were combined, washed with water, then dried over anhydrous Na₂SO₄, and removed the solvents in vacuo. The obtained residue was purified by silica gel column chromatography to give 12.43 g of the corresponding acid compound (rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid) as a yellow solid. Yield: 92%.

A solution of rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid (306 mg, 0.5 mmol) and 1-chloroethyl (2-(2-methoxyethoxy)ethyl)carbonate (510 mg, 2.25 mmol) in dimethylformamide (10 ml) was added NaOH (3 mmol, 975 mg, 6 eq), and stirred overnight under a nitrogen atmosphere. Then, 10 ml of water was added. The mixture was extracted with ethyl acetate (2×15 ml). The organic layers were combined, washed with water, dried over anhydrous Na₂SO₄, and removed the solvents in vacuo. The obtained residue was purified by silica gel column chromatography to give 102 mg of the target compound as a yellow solid. Yield: 26%.

$^1$H NMR (400 MHz, CDCl₃): δ 10.62 (s, 1H), 8.48 (d, J=8 Hz, 1H), 7.79 (d, J=1.6 Hz, 1H), 7.66 (dd, J=8.6 Hz, 1.4 Hz, 1H), 7.56 (s, 1H), 7.47 (t, 1H), 7.33 (d, J=8 Hz, 1H), 7.23 (d, J=9.2 Hz, 1H), 7.19 (d, J=7.6 Hz, 1H), 7.07-6.98 (m, 2H), 4.75-4.68 (m, 1H), 4.50-4.42 (m, 2H), 4.37-4.25 (m, 2H), 3.92 (s, 3H), 3.82 (t, 2H), 3.76-3.50 (m, 9H), 2.18 (bs, 1H), 1.65 (d, J=5.2 Hz, 3H), 1.36-1.22 (m, 1H), 0.95 (s, 9H) (see FIG. 2).

MS: Calcd for $C_{39}H_{45}Cl_2FN_3O_{10}$ ([M+H]$^+$): 804, found: 804.2.

Example 9

Synthesis of Rac-12-oxo-2,5,8,11,13-pentaoxapentadecan-14-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate (rac-SIP-PEG-3)

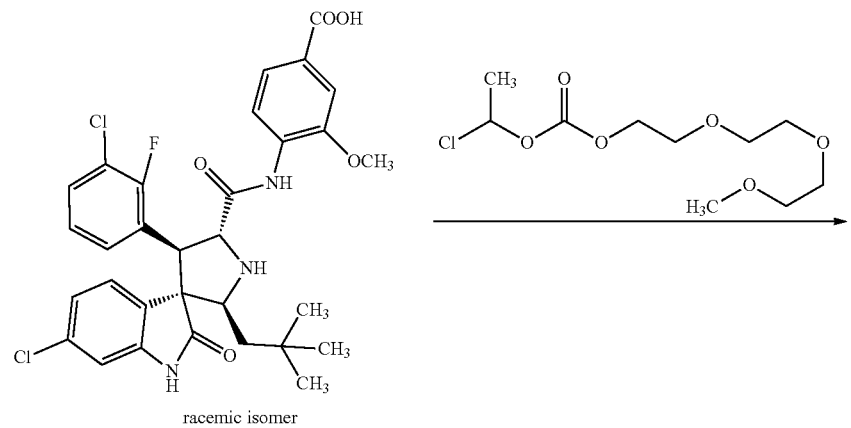

racemic isomer

-continued

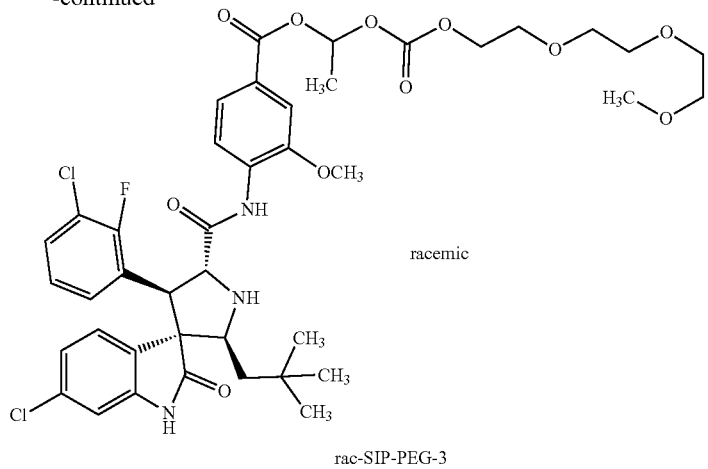

rac-SIP-PEG-3

A solution of rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid (306 mg, 0.5 mmol, synthesized according to the first step in Example 8) and 1-chloroethyl (2-(2-methoxyethoxyethoxy)ethyl)carbonate (609 mg, 2.25 mmol) in dimethylformamide (10 ml) was added NaOH (3 mmol, 975 mg, 6 eq) and stirred overnight under a nitrogen atmosphere; 10 ml of water was then added, and the mixture was extracted with EA ethyl acetate (2×15 ml). The organic layers were combined, washed with water, dried over anhydrous Na$_2$SO$_4$, and removed the solvents in vacuo. The residue obtained was purified by silica gel column chromatography to yield 100 mg of the target compound as a white solid. Yield: 24%.

$^1$H NMR(CDCl$_3$, 400 MHz): δ 10.62 (s, 1H), 8.50 (d, J=4.2 Hz, 1H), 7.79 (d, J=0.6 Hz, 1H), 7.74 (d, J=4.2 Hz, 1H), 7.61 (s, 1H), 7.47 (t, J=6.4 Hz, 1H), 7.33 (d, J=7.6 Hz, 1H), 7.10-7.25 (m, 2H), 7.02 (t, J=7.8 Hz, 1H), 4.70 (d, J=4.8 Hz, 1H), 4.40-4.50 (m, 3H), 3.93 (s, 3H), 3.78-3.80 (m, 2H), 3.72 (d, J=9.0 Hz, 4H), 3.64 (s, 9H), 3.50-3.54 (m, 2H), 3.36 (s, 3H), 1.23-1.35 (m, 1H), 0.95 (s, 9H), 0.90 (s, 1H);

MS: Calcd for C$_{41}$H$_{49}$Cl$_2$FN$_3$O$_{11}$ ([M+H]$^+$): 848, found: 848.3.

Example 10

Synthesis of Compound (4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid-(R)—N,N-dimethyl-1-phenyl-1-ethylamine salt, R-amine salts) having the following structural formula

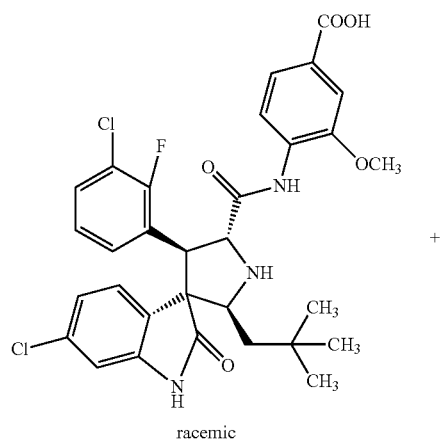

racemic

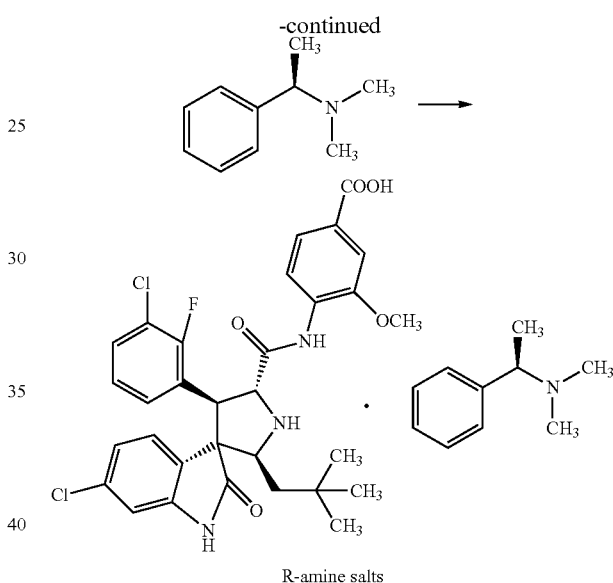

R-amine salts

A mixture of rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid (4.0 g, 6.5 mmol, synthesized according to the first step in Example 8) and (R)—N,N-dimethyl-1-phenylethan-1-amine (1.12 g, 7.49 mmol) was dispersed in ethyl acetate, heated to 60° C. and stirred at this temperature for 2 hours, and then cooled to room temperature and stirred overnight. The precipitated solid was filtered, washed with cold ethyl acetate and dried to give the R-amine salts, 4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid-(R—N,N-dimethyl-1-phenylethan-1-amine salt (2.0 g), as a white solid.

Figure 3:
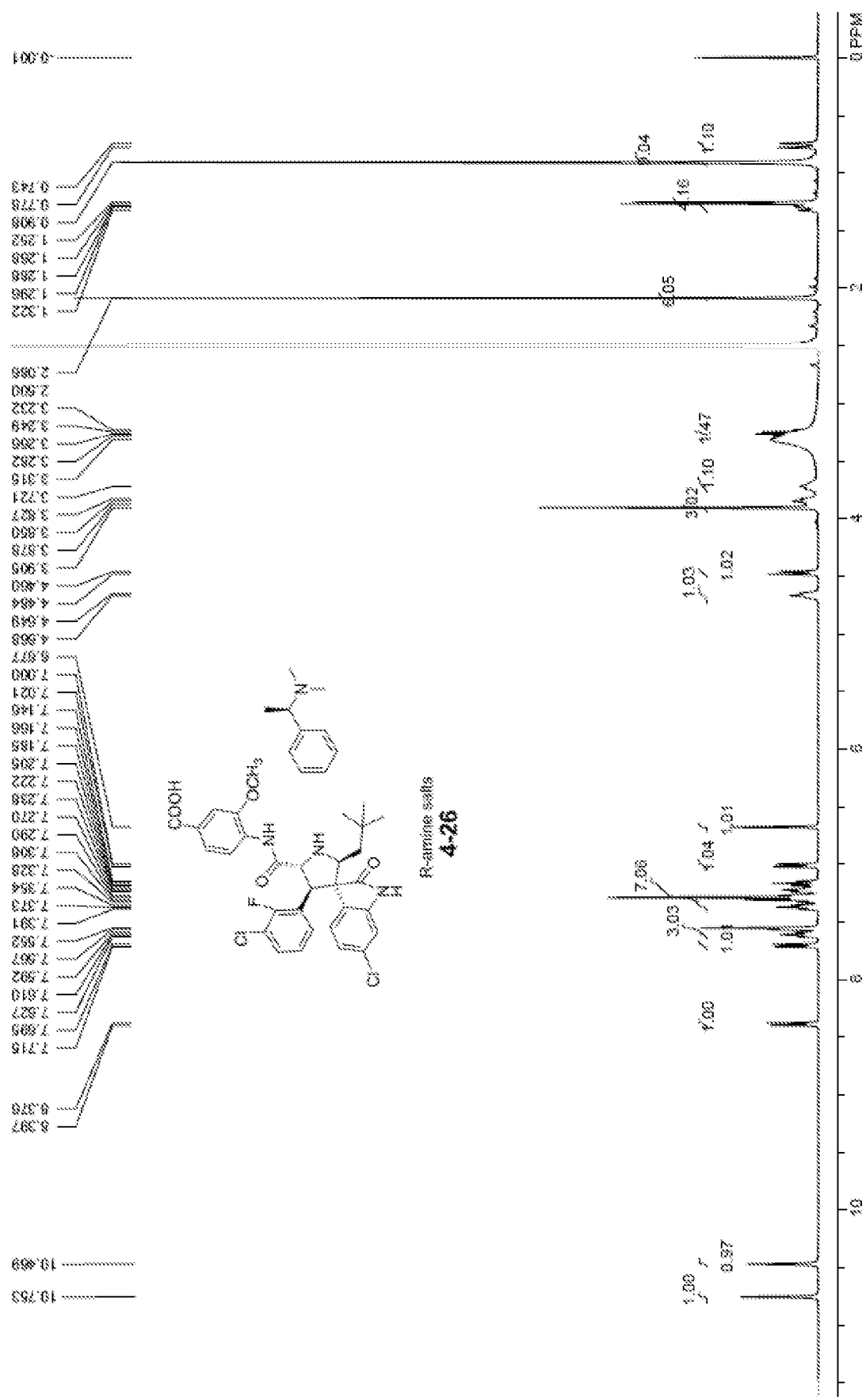
FIG. 3 is a $^1$H NMR spectrum of the compound prepared in Example 10.

$^1$H NMR (d$_6$-DMSO, 400 MHz): δ 10.75 (s, 1H), 10.47 (s, 1H), 8.38 (d, J=8.4 Hz, 1H), 7.70 (d, J=8.0 Hz, 1H), 7.61 (t, J=7.0 Hz, 1H), 7.55-7.58 (m, 2H), 7.37 (t, J=7.4 Hz, 1H), 7.25-7.33 (m, 4H), 7.22 (t, J=6.8 Hz, 1H), 7.17 (t, J=8.0 Hz, 1H), 7.00 (d, J=8.4 Hz, 1H), 6.67 (s, 1H), 4.67 (t, J=7.6 Hz, 1H), 4.47 (d, J=9.6 Hz, 1H), 3.90 (s, 3H), 3.65-3.90 (m, 1H), 3.20-3.40 (m, 2H), 2.08 (s, 6H), 1.29-1.32 (m, 1H), 1.26 (d, J=6.8 Hz, 3H), 0.91 (s, 9H), 0.76 (d, J=14 Hz, 1H) (see FIG. 3).

Example 11

Synthesis of Chiral-12-oxo-2,5,8,11,13-pentaoxa-pentadecan-14-yl-4-((2'S,3R,4'S,5'R)-6-chloro-4'-(3-chloro-2-fluorophenyl)-2'-neopentyl-2-oxospiro [indoline-3,3'-pyrrolidine]-5'-carboxamido)-3-methoxybenzoate (chiral-R-SIP-PEG-3)

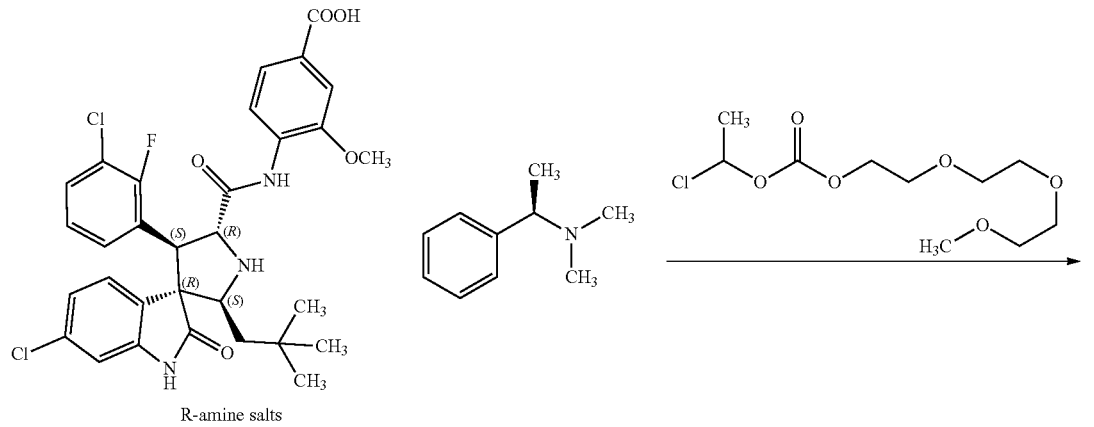

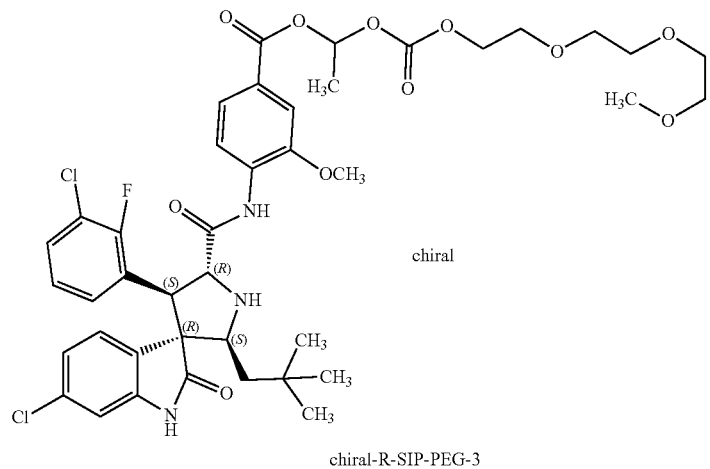

A solution of 4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid-(R)—N,N-dimethyl-1-phenylethan-1-amine salt (382 mg, 0.5 mmol) and 1-chloroethyl (2-(2-methoxyethoxyethoxy)ethyl)carbonate (609 mg, 2.25 mmol) in dimethylformamide (10 ml) was added with NaOH (3 mmol, 975 mg, 6 eq) and stirred overnight under a nitrogen atmosphere; then 10 ml of water was added, and the mixture was extracted with ethyl acetate (2×15 ml). The organic layers were combined, washed with water, dried over anhydrous $Na_2SO_4$, and removed the solvents in vacuo. The residue obtained was purified by silica gel column chromatography to give 98 mg of the target compound as a white solid. Yield: 23%. $[\alpha]^{20}_D = -138°$ (0.1 g/100 ml, $CH_3OH$).

Figure 4:
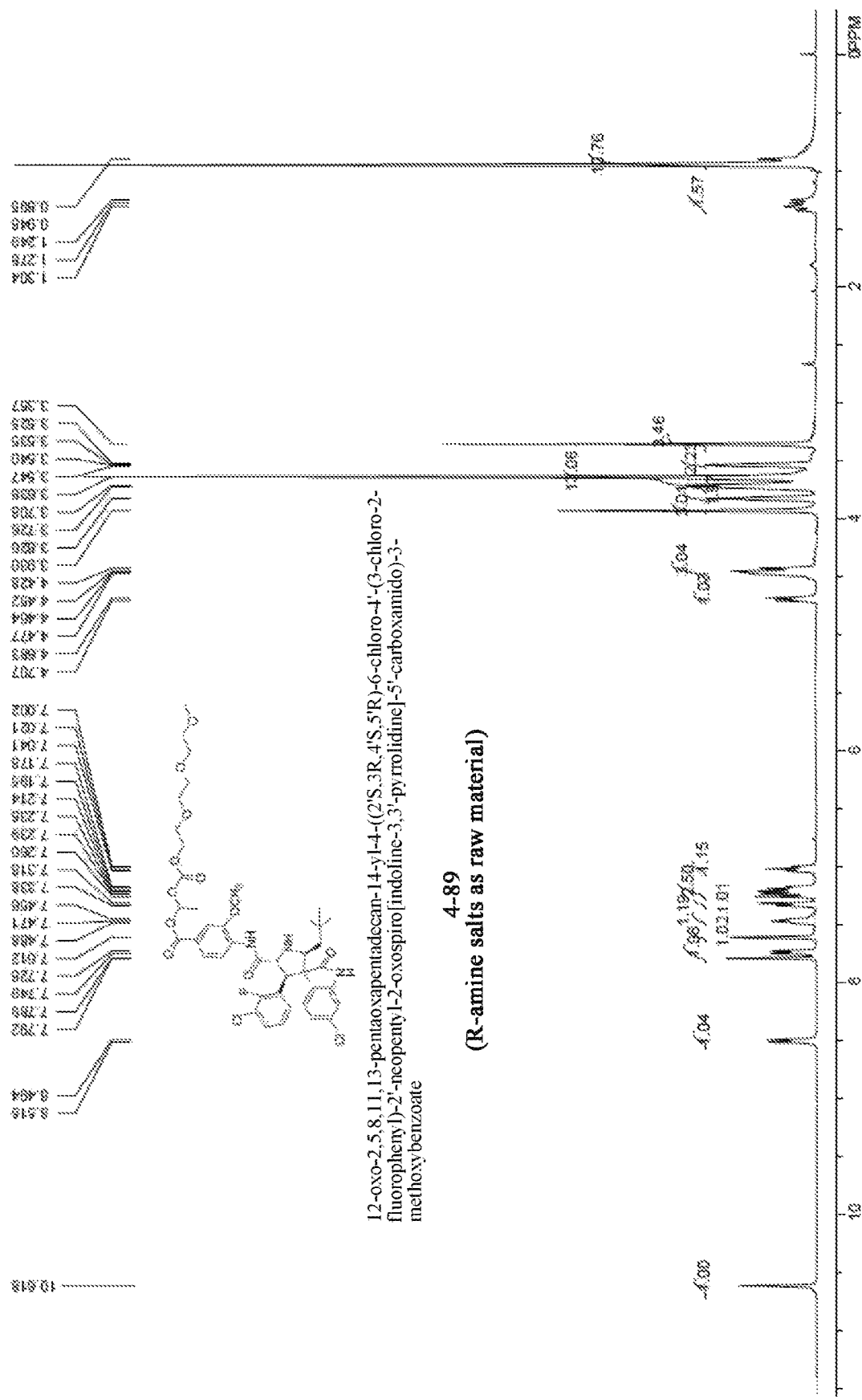
FIG. 4 is a $^1$H NMR spectrum of the compound of the invention prepared in Example 11.

$^1$H NMR ($CDCl_3$, 400 MHz): δ 10.62 (s, 1H), 8.51 (d, J=8.8 Hz, 1H), 7.92 (s, 1H), 7.73 (d, J=8.4 Hz, 1H), 7.60 (s, 1H), 7.47 (t, J=6.8 Hz, 1H), 7.33 (d, J=7.6 Hz, 1H), 7.10-7.25 (m, 2H), 7.02 (t, J=7.8 Hz, 1H), 4.68-4.80 (m, 1H), 4.40-4.50 (m, 3H), 3.93 (s, 3H), 3.80-3.88 (m, 2H), 3.70-3.80 (m, 4H), 3.60-3.70 (m, 9H), 3.50-3.58 (m, 2H), 3.36 (s, 3H), 1.23-1.35 (m, 1H), 0.95 (s, 9H), 0.85-0.90 (m, 1H) (see FIG. 4);

MS: Calcd for $C_{41}H_{49}Cl_2FN_3O_{11}$ ([M+H]$^+$): 848, found: 848.3.

Example 12

Synthesis of Rac-24-oxo-2,5,8,11,14,17,20,23,25-nonoxaheptacosan-26-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate (rac-SIP-PEG-7)

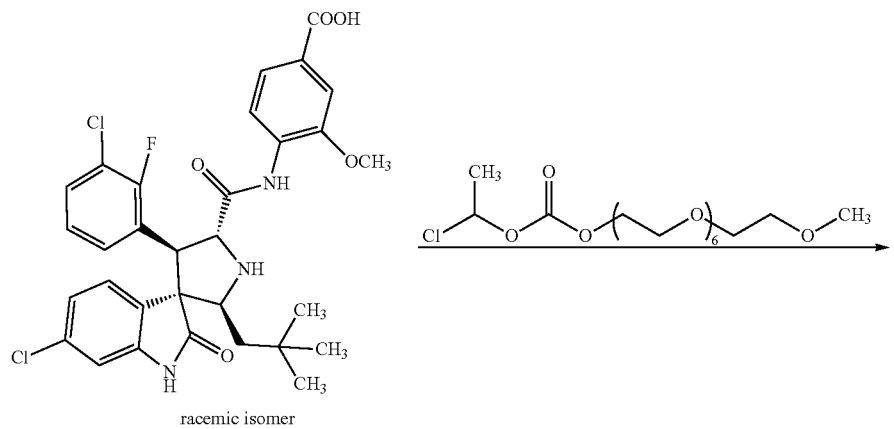

A solution of rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid (306 mg, 0.5 mmol) and 1-chloroethyl (2,5,8,11,14,17,20-heptaoxadocosan-22-yl)carbonate (1.00 g, 2.25 mmol) in dimethylformamide (10 ml) was added NaOH (3 mmol, 975 mg, 6 eq) and stirred overnight at a nitrogen atmosphere; then 10 ml of water was added, and the mixture was extracted with ethyl acetate (2×15 ml). The organic layers were combined, washed with water, dried over anhydrous $Na_2SO_4$, and removed the solvents in vacuo. The residue obtained was purified by silica gel column chromatography to give 77 mg of the target compound. Yield: 15%.

Calculated molecular formula (M+H): $C_{49}H_{65}Cl_2FN_3O_{15}$; calculated molecular weight: 1024.3777, HRMS ($C_{49}H_{65}Cl_2FN_3O_{15}$) found: 1024.3772.

Example 13

Synthesis of Rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid methoxy polyethylene glycol 1000 carbonate (rac-SIP-MPEG-1000)

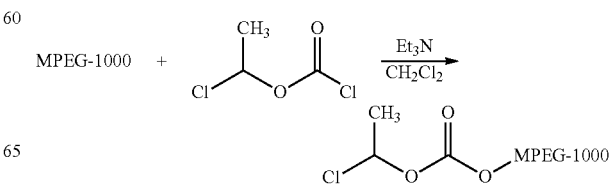

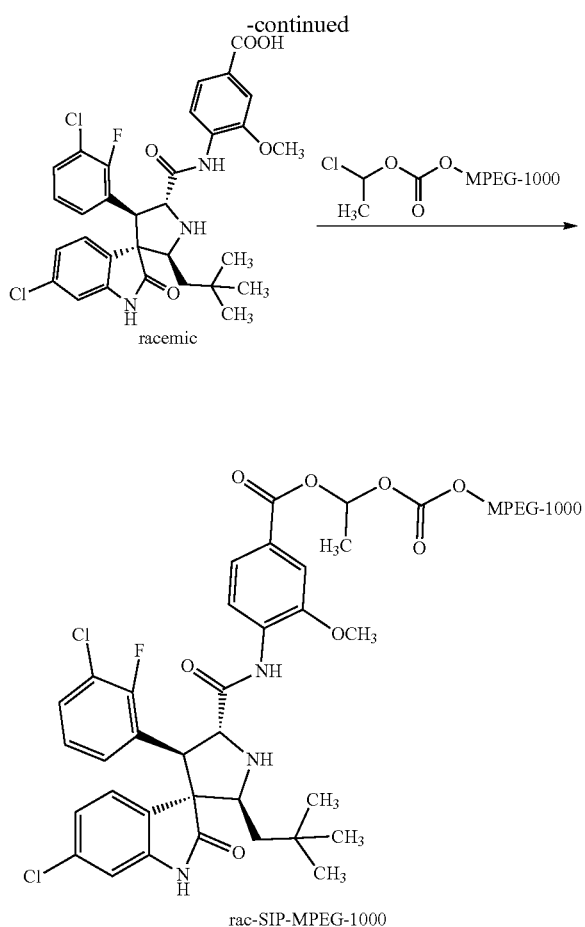

Example 14

Synthesis of Rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid methoxy polyethylene glycol 2000 carbonate (rac-SIP-MPEG-2000)

Methoxy polyethylene glycol 1000 [MPEG-1000 (CAS: 9004-74-4, average molecular weight Mn=1000, TCI), 1.0 g, 1.0 mmol] and triethylamine (505 mg, 5.0 mmol) were dissolved in dichloromethane (10 ml). To the solution 1-chloroethyl chloroformate (715 mg, 5.0 mmol) was added dropwise under an ice-bath condition. The resulting mixture was stirred and reacted for 24 hours, then washed with water, extracted, and dried to give 1-chloroethylmethoxy polyethylene glycol 1000 carbonate, which was used directly for the following reaction.

Figure 5:
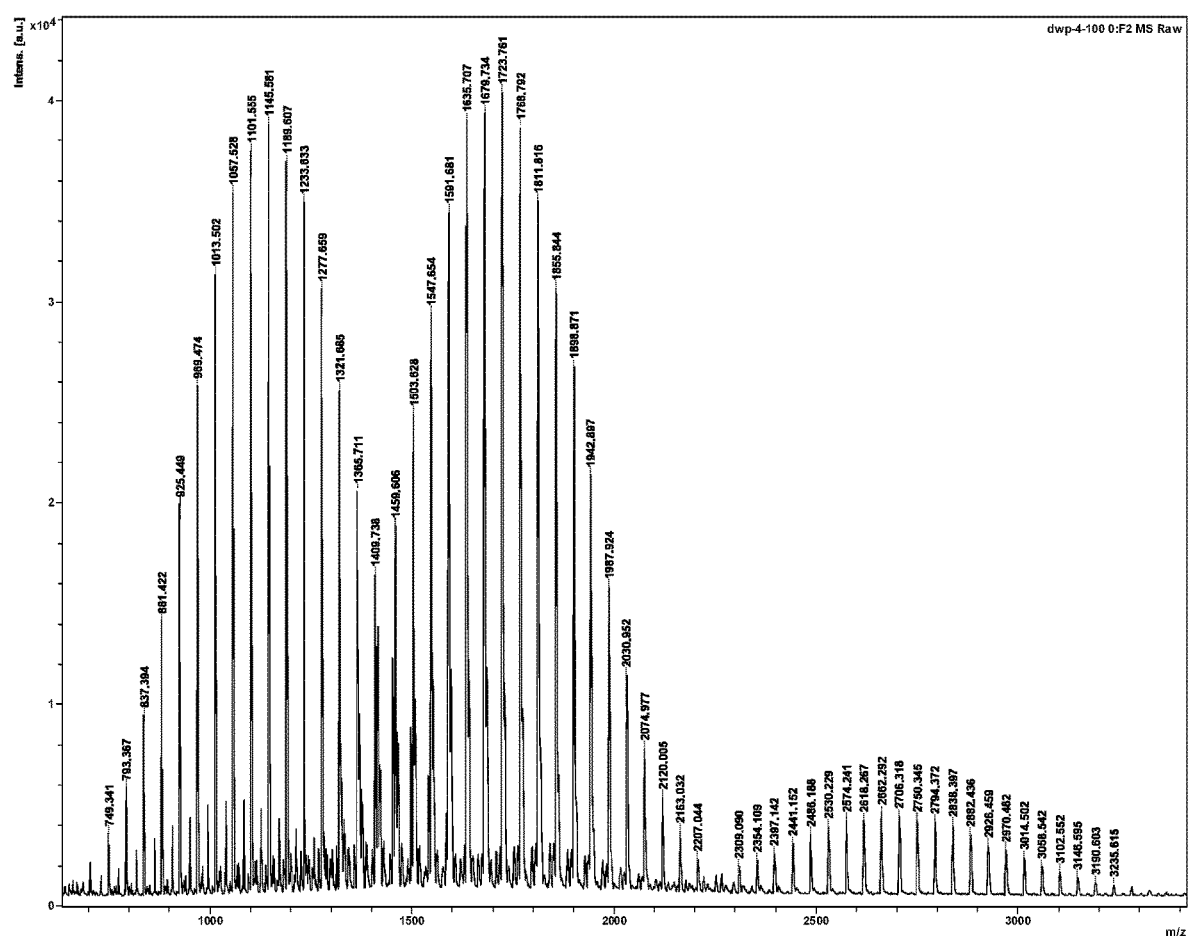
FIG. 5 is a spectrum from matrix-assisted laser desorption/ionization time of flight mass spectrometry (MALDI-TOF-MS) of the compound of the invention prepared in Example 13.

A solution of rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid (306 mg, 0.5 mmol) and 1-chloroethylmethoxypolyethylene glycol 1000 carbonate (2.53 g, 2.25 mmol) in dimethylformamide (10 ml) was added NaOH (3 mmol, 975 mg, 6 eq) and stirred overnight under a nitrogen atmosphere; 10 ml of water was then added, and the mixture was extracted with ethyl acetate (2×15 ml). The organic layers were combined, washed with water, dried over anhydrous $Na_2SO_4$, and removed the solvents in vacuo. The residue obtained was purified by preparative liquid chromatography to give 128 mg of the target compound. Yield: 15%. MALDI-TOF MS: about 1700 (see FIG. 5).

Chloroethyl methoxy polyethylene glycol 2000 carbonate can be prepared from the raw material methoxy polyethylene glycol 2000 (CAS: 9004-74-4, average molecular weight $M_n$=2000, Sigma-Aldrich) according to the procedures for synthesizing 1-chloroethyl methoxy polyethylene glycol 1000 carbonate in Example 13.

Figure 6:
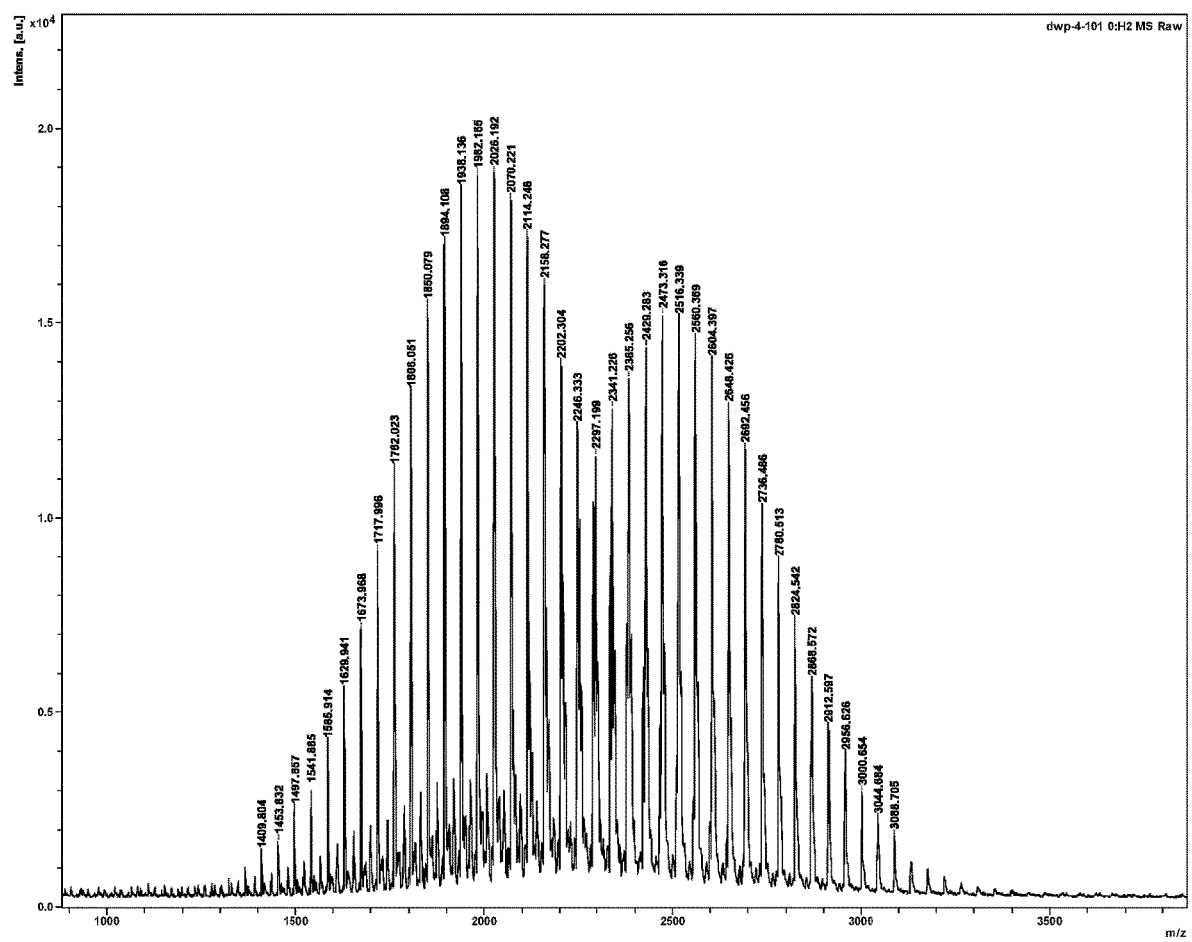
FIG. 6 is a spectrum from matrix-assisted laser desorption/ionization time of flight mass spectrometry (MALDI-TOF-MS) of the compound of the invention prepared in Example 14.

A solution of rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid (306 mg, 0.5 mmol) and 1-chloroethylmethoxypolyethylene glycol 2000 carbonate (4.80 g, 2.25 mmol) in dimethylformamide (10 ml) was added NaOH (3 mmol, 975 mg, 6 eq), and stirred overnight under a nitrogen atmosphere; then 10 ml of water was added, and the mixture was extracted with ethyl acetate (2×15 ml). The organic layers were combined, washed with water, dried over anhydrous $Na_2SO_4$, and removed the solvents in vacuo. The residue obtained was purified by preparative liquid chromatography to give 220 mg of the target compound. Yield: 17%. MALDI-TOF MS: about 2600 (see FIG. 6).

Examples 15-17

Synthesis of Racemic Compounds having the Following Structural Formulas (Synthetic routes are as described in Example 8)

Example 15

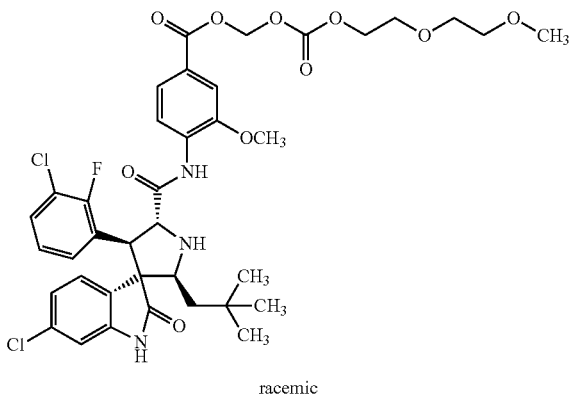

racemic

MS: Calculated (M+H)+: 790.
MS: found (M+H)+: 790.2.

Example 16

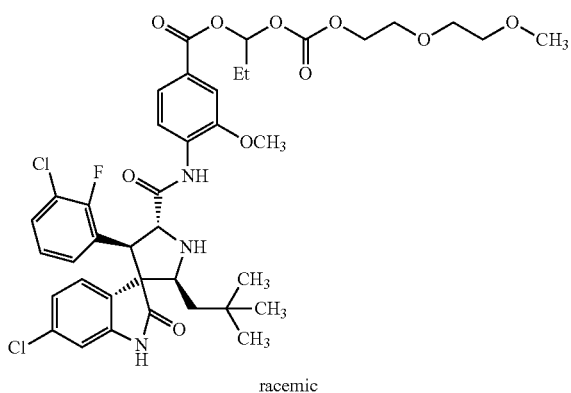

racemic

MS: Calculated (M+H)+: 818.
MS: found (M+H)+: 818.3.

Example 17

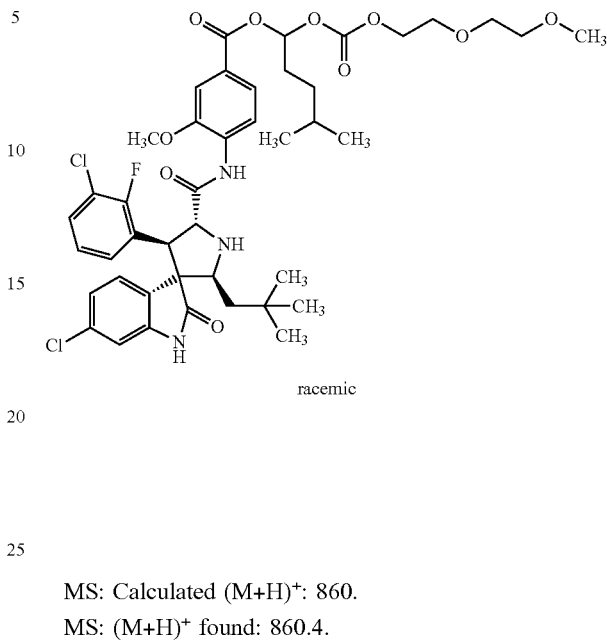

racemic

MS: Calculated (M+H)+: 860.
MS: (M+H)+ found: 860.4.

Examples 18-20

Synthesis of Racemic Compounds having the Following Structural Formulas (Synthesis routes are as described in Examples 9 and 12)

Example 18

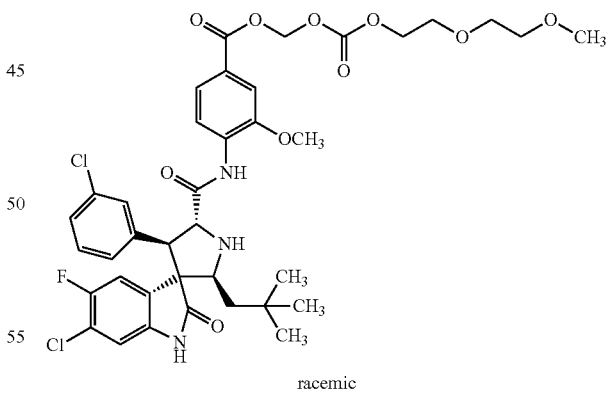

racemic

MS: Calculated (M+H)+: 790.
MS: found (M+H)+: 790.3.

Example 19

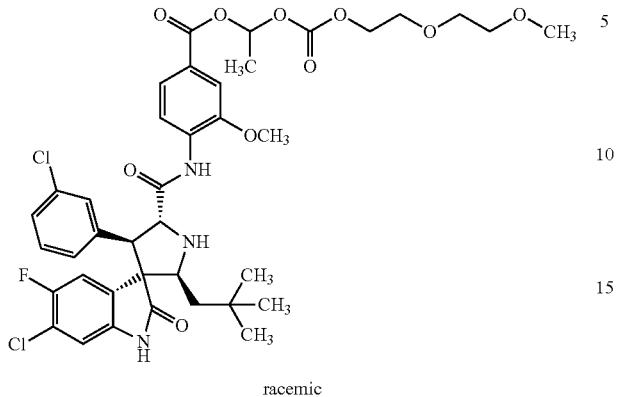

racemic

MS: Calculated (M+H)$^+$: 804.
MS: found (M+H)$^+$: 804.3.

Example 20

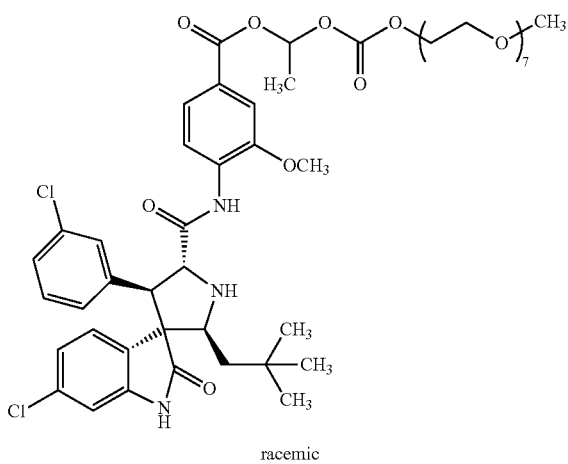

racemic

MS: Calculated (M+H)$^+$: 1006.
MS: found (M+H)$^+$: 1006.4.

EXPERIMENTAL EXAMPLES

Improvement Effect of the Compounds of the Present Invention on Water Solubility I. Experimental Objective To examine the improvement effect of the compounds of the present invention on water solubility of the spirocyclic indolone compounds via the polyethylene glycol carbonate structure.

II. Experimental Method 30.00 Mg rac-SIP (rac-spiroindolinone pyrrolidinecarboxamide, Org. Process Res. Dev. 2013; 17(2): 247-256) was accurately weighed as a reference, placed in a 10-ml volumetric flask, dissolved in and diluted to volume with acetonitrile, to prepare a rac-SIP mother liquid at a concentration of 3.00 mg/ml, stored at low temperature and protected from light for use.

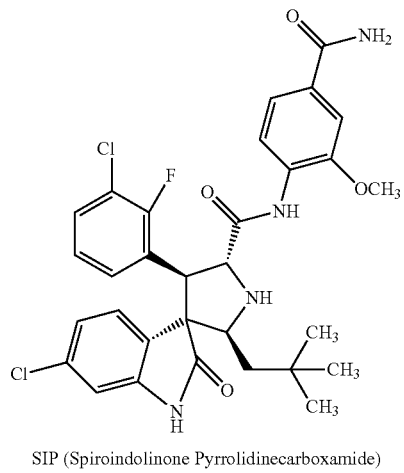

SIP (Spiroindolinone Pyrrolidinecarboxamide)

Chromatographic conditions: Column: Iinertsil ODS-3 column (4.6×150 mm, 5 μm); Mobile phase: acetonitrile-20% phosphoric acid solution (40:60, V/V); Flow rate: 1 ml/min; Detection wavelength: 286 nm; Injection volume: 20 μl; Temperature: room temperature. Under these chromatographic conditions, an appropriate concentration of rac-SIP reference solution was injected to determine the retention time of the rac-SIP peak, which was 4.5 min, and that the main peak was not interfered by the impurities.

The rac-SIP reference mother liquor was precisely measured in a 10-ml volumetric flask, diluted to volume with acetonitrile, and shake well to obtain a series of standard solutions with concentrations of 0.1, 0.5, 1.0, 2.0, and 3.0 μg/ml, respectively. Detection was made under the above chromatographic conditions. The peak area was recorded, and the peak area (Y) was plotted against the concentration (X) to obtain a regression equation (Y=88.85X+0.2221 ($r^2$=0.9998), and the concentrations of the samples were calculated according to this equation.

Excess amounts of rac-SIP, rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid (rac-SIP-acid) (a precursor of rac-SIP-PEG-2, see the reaction in Example 8), rac-SIP-PEG-2 (i.e., the compound of Example 8), rac-SIP-PEG-3 (i.e., the compound of Example 9), chiral-R-SIP-PEG-3 (i.e., the compound of Example 11), rac-SIP-PEG-7 (i.e., the compound of Example 12), rac-SIP-MPEG-1000 (i.e., the compound of Example 13), and rac-SIP-MPEG-2000 (i.e., the compound of Example 14), were each placed in a test tube with a stopper, added an appropriate amount of water, sonicated until no longer to be dissolved, placed and shaken in an oscillator (100 r/min) at (25±1) ° C. for 24 hours. After the dissolving reached equilibrium, saturated solution of each compound was taken out, placed in a centrifuge and centrifuged at 10 000 r/min for 10 min. The supernatant was accurately aspirated, and quantitatively diluted with acetonitrile before injected for assay. The solubility in water of these different derivatives was approximately calculated by the SIP standard curve.

III. Experimental Results

The results from the solubility test showed that rac-SIP and rac-SIP-acid have a very low solubility in water (<0.1 mg/ml) and are nearly insoluble in water; while rac-SIP-PEG-2 (i.e., the compound of Example 8) has a solubility >0.4 mg/ml, rac-SIP-PEG-3 (i.e., the compound of Example 9) has a solubility >3 mg/ml, chiral-R-SIP-PEG-3 (i.e., the compound of Example 11) has a solubility >8 mg/ml, rac-SIP-PEG-7 (i.e., the compound of Example 12) has a solubility of 30 mg/ml, rac-SIP-MPEG-1000 (i.e., the compound of Example 13) has a solubility >100 mg/ml, and rac-SIP-MPEG-2000 (i.e., the compound of Example 14) has a solubility >100 mg/ml. It can be concluded that as the length of PEG (i.e., —$CH_2$—$CH_2$—O—) increases, the solubility becomes better.

Inhibitory Effect of the Compounds of the Present Invention on the Growth of SJSA-1 Xenografted Tumor in Nude Mice I. Experimental Objective To examiner the inhibitory effect of a known chiral compound, rac-SIP, and the chiral compounds of the present invention, rac-SIP-PEG-2 (i.e., the compound of Example 8), rac-SIP-PEG-3 (i.e., the compound of Example 9), chiral-R-SIP-PEG-3 (i.e., the compound of Example 11), rac-SIP-PEG-7 (i.e., the compound of Example 12), rac-SIP-MPEG-2000 (i.e., the compound of Example 14) on the growth of SJSA-1 xenografted tumor in nude mice.

II. Experimental Animals

72 Female Balb/c/nu nude mice (weighting 15-19 g) were provided by Beijing Huafukang BioScience Co., Inc. Certificate No.: SOCK (Beijing) 2014-0004.

III. Experimental Drugs and Reagents

1. Drugs

Doxorubicin: a positive control drug rac-SIP: (Org. Process Res. Dev. 2013; 17(2):247-256) milky white powder rac-SIP-PEG-2 (i.e., the compound of Example 8): white powder rac-SIP-PEG-3 (i.e., the compound of Example 9): white powder chiral-R-SIP-PEG-3 (i.e., the compound of Example 11): white powder rac-SIP-PEG-7 (i.e., the compound of Example 12): white powder rac-SIP-MPEG-2000 (i.e., the compound of Example 14): white powder 2. Drug Preparation Method Doxorubicin: prepared in sterile physiological saline at a concentration of 0.3 mg/ml; the administration dosage was 3.0 mg/kg; and the administration volume was 10 ml/kg.

rac-SIP: prepared in a solvent consisting of 4% DMA, 30% PEG400, and 66% (by volume) sterile distilled water to a solution with a concentration of 1.5 mg/ml; the administration dosage was 30.0 mg/kg, and the administration volume was 20 ml/kg.

rac-SIP-PEG-2: prepared in a solvent consisting of polyoxyethylene castor oil:95% ethanol:sterile physiological saline (1.5:1.5:7 by volume) to drug solutions with concentrations of 1.5 mg/ml and 3.0 mg/ml. The administration dosages were 15.0 mg/kg and 30.0 mg/kg. The administration volume was 10 ml/kg.

rac-SIP-PEG-3: prepared in sterile physiological saline to a solution with a concentration of 3.0 mg/ml. The administration dose was 30.0 mg/kg. The administration volume was 10 ml/kg.

chiral-R-SIP-PEG-3: prepared in sterile physiological saline to a solution with a concentration of 3.0 mg/ml. The administration dose was 30.0 mg/kg. The administration volume was 10 ml/kg.

rac-SIP-PEG-7: prepared in sterile physiological saline to a solution with a concentration of 3.0 mg/ml. The administration dose was 30.0 mg/kg. The administration volume was 10 ml/kg.

rac-SIP-MPEG-2000: prepared in sterile physiological saline to a solution with a concentration of 5.0 mg/ml. The administration dose was 50.0 mg/kg. The administration volume was 10 ml/kg.

3. Doses and Routes of Administration:

Doxorubicin: at a dose of 3.0 mg/kg, administered intraperitoneally, once every other day, for a total of 6 times.

rac-SIP: at a dose of 30.0 mg/kg, administered by gavage, once a day, 6 times a week, for a total of 9 times.

rac-SIP-PEG-2: at a dose of 30.0 mg/kg, administered intraperitoneally, once a day, 6 times a week, for a total of 9 times.

rac-SIP-PEG-3: at a dose of 30.0 mg/kg, administered intraperitoneally, once a day, 6 times a week, for a total of 9 times.

chiral-R-SIP-PEG-3: at a dose of 30.0 mg/kg, administered intraperitoneally, once a day, 6 times a week, for a total of 9 times.

rac-SIP-PEG-7: at a dose of 30.0 mg/kg, administered intraperitoneally, once a day, 6 times a week, for a total of 9 times.

rac-SIP-mPEG-2000: at a dose of 50.0 mg/kg, administered intraperitoneally, once a day, 6 times a week, for a total of 9 times.

4. SJSA-1 Cells: Purchased from Shanghai Fuxiang Biotechnology Co., Ltd.

5. Other Reagents: Polyoxyethylene Castor Oil (Aladdin Reagent Co., Ltd. CAS: 61791-12-6).

IV. Experimental Procedures

Tumor cells (SJSA-1) were harvested under aseptic conditions, and were adjusted to a cell density of $1\times10^7$ cells/ml with sterile physiological saline. 0.2 ml was inoculated under the skin of the axilla of nude mice, and the tumor was grown to have a diameter of 1 cm. The tumor was removed under aseptic conditions and cut into tumor masses with a size of 2.0 mm×2.0 mm, and evenly inoculated under the skin of the axilla of the nude mice. When the tumor volume reached about 250 mm$^3$ (8 days after inoculation), the animals were administered in groups with 9 mice in each group, and the animals with poor tumor growth were excluded. The control group used physiological saline as a control. Dose groups included doxorubicin at a dose of 3.0 mg/kg; rac-SIP at a dose of 30.0 mg/kg dose group; rac-SIP-PEG-2, rac-SIP-PEG-3, chiral-R-SIP-PEG-3 and rac-SIP-PEG-7 each at a dose of 30.0 mg/kg and rac-SIP-MPEG-2000 at a dose of 50.0 mg/kg. Body weight was weighted 3 times a week, and the length a and the width b of the tumor were measured with a vernier caliper, and the volume of the tumor was calculated according to the formula $V=a\times b^2/2$, where a is the length of the tumor and b is the width of the tumor. 21 Days after the inoculation, the nude mice were dislocated and photographed, and then the tumor was peeled off, weighed and photographed. RTV (relative tumor volume) and tumor inhibition rate were calculated. At the same time, the peripheral blood of nude mice was taken to count blood cells.

V. Data Processing

The data were processed by EXCEL software and expressed by Mean±SD, and the inter-group analysis was statistically processed using t test.

VI. Results

1. Effect of Solubility on Dosage Form

As can be seen from the drug preparation method, the series of rac-SIP-PEG compounds (Example 8, Example 9, Example 11, Example 12 and Example 14) have water solubility greater than the PEG-free compounds, rac-SIP and rac-SIP-acid; and the water solubility increases with the extension of PEG. Example 9, Example 11, Example 12 and Example 14 exhibited greater water solubility than Example 8, and could be directly dissolved in physiological saline, being more suitable for intravenous administration, and thus avoiding gastrointestinal side effects of oral drugs.

2. Evaluation of the Efficiency for Tumor Suppression

Figure 8:
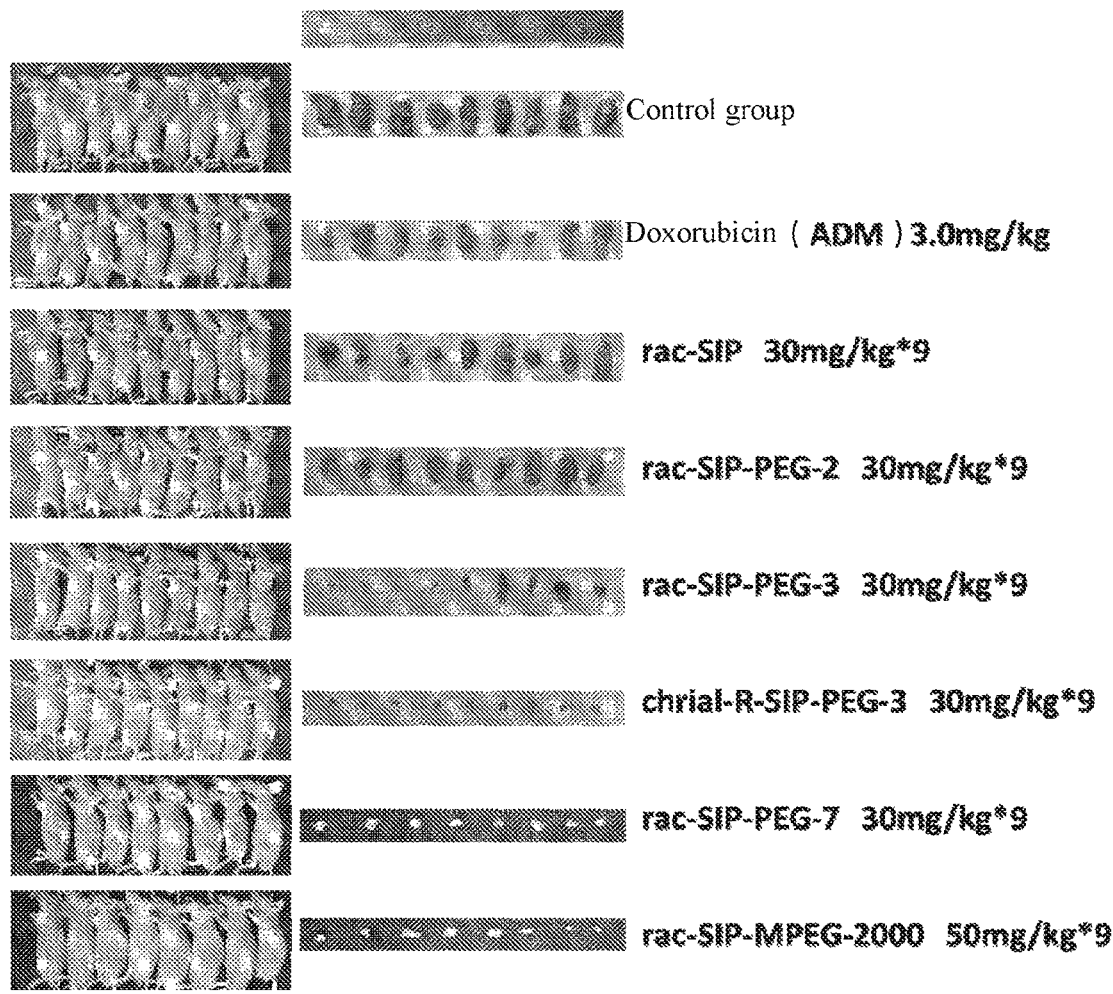
FIG. 8 is a graph showing the inhibitory effect of doxorubicin, rac-SIP, rac-SIP-PEG-2 (i.e., the compound of Example 8), rac-SIP-PEG-3 (i.e., the compound of Example 9), chiral-R-SIP-PEG-3 (i.e., the compound of Example 11), rac-SIP-PEG-7 (i.e., the compound of Example 12), and rac-SIP-MPEG-2000 (i.e., the compound of Example 14) on the growth of SJSA-1 xenografted tumor in nude mice.
Figure 9:
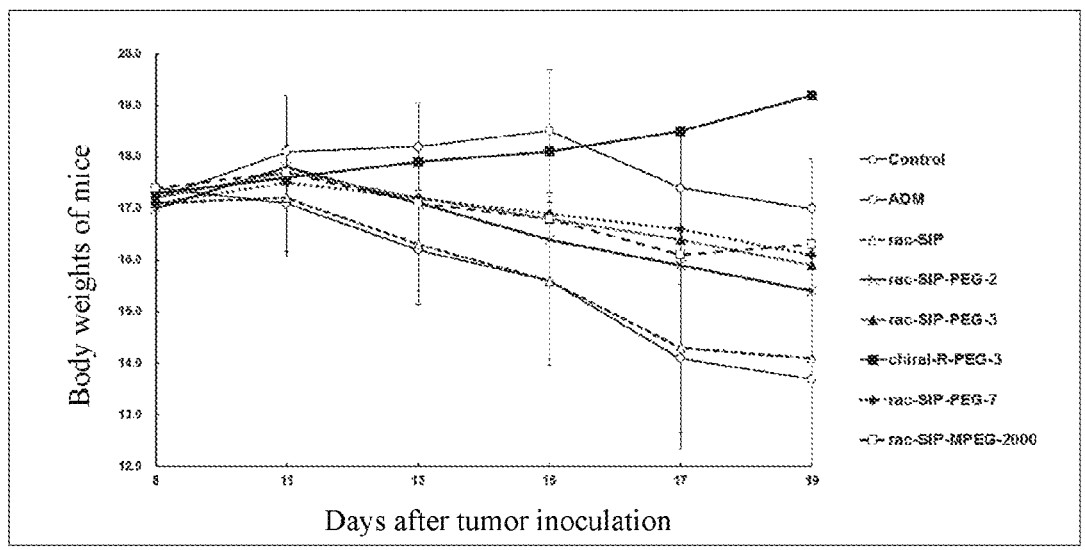
FIG. 9 is a curve graph showing the effect of doxorubicin, rac-SIP, rac-SIP-PEG-2 (i.e., the compound of Example 8), rac-SIP-PEG-3 (i.e., the compound of Example 9), chiral-R-SIP-PEG-3 (i.e., the compound of Example 11), rac-SIP-PEG-7 (i.e., the compound of Example 12), and rac-SIP-MPEG-2000 (i.e., the compound of Example 14) on the body weights of SJSA-1 implanted nude mice.

The compounds of the present invention, due to the presence of PEG, exhibited a significantly greater inhibitory effect on tumor growth than the PEG-free compound SIP; wherein rac-SIP-PEG-2 administered by injection at a dose of 30.0 mg/kg exhibited a slightly better inhibitory effect on tumor growth than the PEG-free rac-SIP given by gastrointestinal administration; rac-SIP-PEG-3, chiral-R-PEG-3 and rac-SIP-PEG-7 at a dose of 30.0 mg/kg, and rac-SIP-MPEG-2000 at a dose of 50.0 mg/kg administered by injection exhibited a stronger inhibitory effect on tumor growth than the PEG-free rac-SIP given by gastrointestinal administration. Calculated on the basis of the relative tumor volume, the inhibition rates were 55.36% for rac-SIP-PEG-2, 90.79% for rac-SIP-PEG-3, 97.9% for chiral-R-PEG-3, 96.38% for rac-SIP-PEG-7, and 96.02% for rac-SIP-MPEG-2000, but only 54.89% for SIP which was given by oral administration; and calculated on the basis of tumor weight, the tumor inhibition rates were 50.55% for rac-SIP-PEG-2, 92.86% for rac-SIP-PEG-3, 97.84% for chiral-R-PEG-3, 97.06% for rac-SIP-PEG-7, and 96.70% for rac-SIP-MPEG-2000, but only 49.69% for SIP which was given by oral administration (see Table 1, and FIGS. 7, 8). Compared with the saline control group, the body weight in each of the dose groups was decreased, except the body weight in the chiral-R-PEG-3 dose group was increased, which were statistically significant (see Table 1, FIG. 9). It can be concluded that the spirocyclic indolone polyethylene glycol carbonate compounds (SIP-PEG) have more potent antitumor activity than the unesterified spirocyclic indolone (SIP).

3. Evaluation of Side Effects

Figure 7:
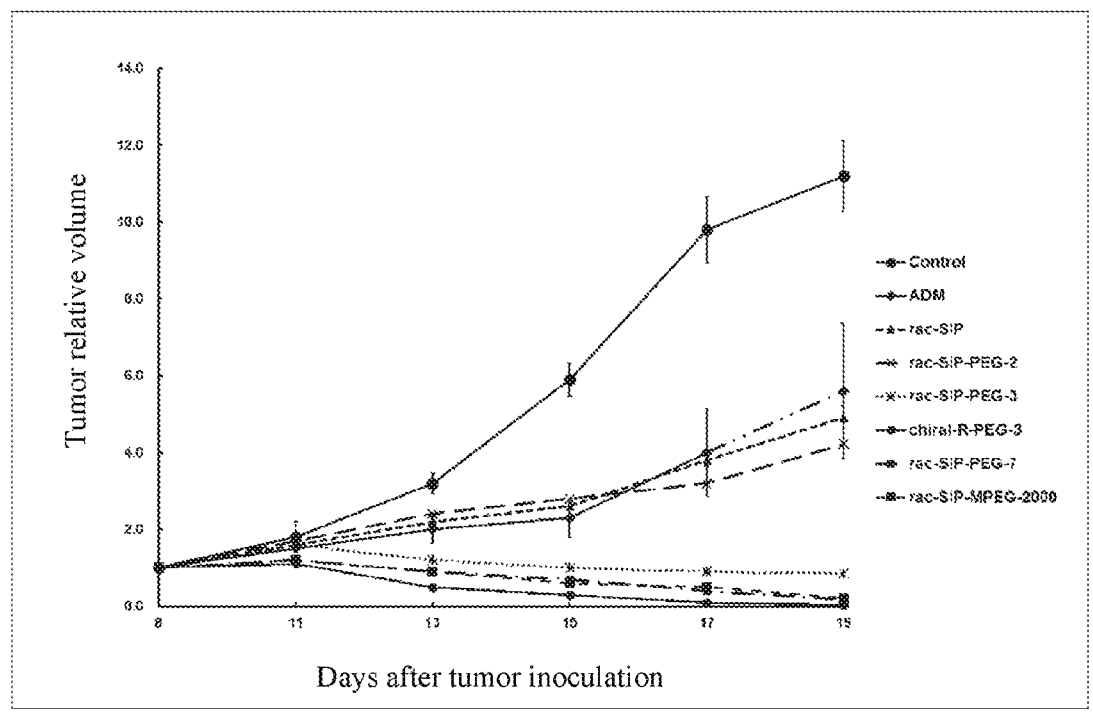
FIG. 7 is a curve graph showing the inhibitory effect of doxorubicin, rac-SIP, rac-SIP-PEG-2 (i.e., the compound of Example 8), rac-SIP-PEG-3 (i.e., the compound of Example 9), chiral-R-SIP-PEG-3 (i.e., the compound of Example 11), rac-SIP-PEG-7 (i.e., the compound of Example 12), and rac-SIP-MPEG-2000 (i.e., the compound of Example 14) on the growth of SJSA-1 xenografted tumor in nude mice against relative tumor volumes.

Compared with the solvent control group, the body weight was decreased by about 9.4% for rac-SIP-PEG-2; the body weight was decreased by about 7.5% for rac-SIP-PEG-3; the body weight was increased by about 11% for chiral-R-PEG-3; the body weight was decreased by about 6.4% for rac-SIP-PEG-7; the body weight was decrease d by about 5.2% for rac-SIP-MPEG-2000; and the body weight was decreased by about 18% for SIP which was given by oral administration, which were statistically significant (see Table 1, FIG. 7). Therefore, it can be concluded that the spirocyclic indolone polyethylene glycol carbonate compounds (SIP-PEG) have less toxic side effects than the unesterified spirocyclic fluorenone (SIP).

TABLE 1

Inhibitory effect of a series of rac-SIP-PEG compounds on the growth of SJSA-1 xenografted tumor in nude mice

| Groups | Dose (mg/kg) | Number of Animals (n) | Body Weights X ± SD (g) Start | Body Weights X ± SD (g) End | Tumor volumes X ± SD(mm$^3$) Start | Tumor volumes X ± SD(mm$^3$) End | Inhibition rate (%) | Weights of Tumor X ± SD (g) | Inhibition rate (%) |
|---|---|---|---|---|---|---|---|---|---|
| Control | — | 9/9 | 17.2 ± 1.0 | 17.0 ± 0.8 | 247.8 ± 27.4 | 2823.6 ± 591.5 | | 2.73 ± 0.43 | |
| Doxorubicin ADM | 3.0 | 9/9 | 17.4 ± 0.7 | 13.7 ± 0.7*** | 241.1 ± 46.6 | 1401.1 ± 658.2*** | 50.38 | 1.41 ± 0.66*** | 48.27 |
| rac-SIP | 30.0 | 9/9 | 17.1 ± 0.8 | 14.1 ± 1.6*** | 249.4 ± 59.5 | 1273.7 ± 506.9*** | 54.89 | 1.37 ± 0.55*** | 49.69 |
| rac-SIP-PEG-2 | 30.0 | 9/9 | 17.0 ± 1.1 | 15.4 ± 1.0** | 242.6 ± 49.9 | 1260.8 ± 597.6*** | 55.36 | 1.35 ± 0.64*** | 50.55 |
| rac-SIP-PEG-3 | 30.0 | 9/9 | 17.2 ± 0.7 | 15.9 ± 1.8** | 246.4 ± 23.6 | 260.1 ± 219.3*** | 90.79 | 0.20 ± 0.20*** | 92.86 |
| chiral-R-SIP-PEG-3 | 30.0 | 9/9 | 17.3 ± 0.9 | 19.2 ± 1.2** | 252.9 ± 68.3 | 59.4 ± 46.3*** | 97.90 | 0.06 ± 0.05*** | 97.84 |
| rac-SIP-PEG-7 | 30.0 | 9/9 | 17.1 ± 0.7 | 16.1 ± 1.6** | 247.6 ± 57.4 | 93.2 ± 65.2*** | 96.38 | 0.08 ± 0.14*** | 97.06 |
| rac-SIP-MPEG-2000 | 50.0 | 9/9 | 17.4 ± 1.0 | 16.3 ± 1.5** | 251.3 ± 39.8 | 102.5 ± 58.5*** | 96.02 | 0.09 ± 0.09*** | 96.70 |

*p < 0.05,
**p < 0.01,
***p < 0.001, vs. control group.

What is claimed is:

1. A spirocyclic indolone polyethylene glycol carbonate compound represented by the following general formula I, a stereoisomer thereof, or a pharmaceutically acceptable salt thereof:

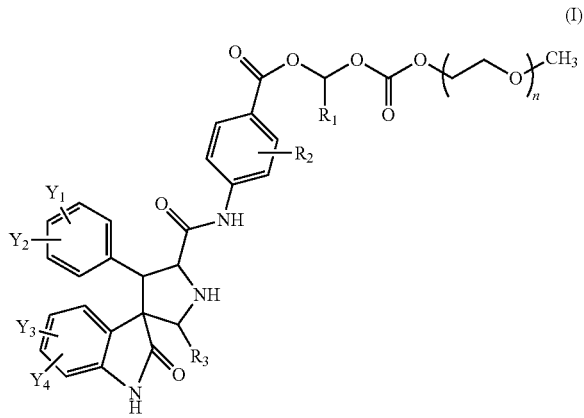

(I)

wherein $Y_1$, $Y_2$, $Y_3$, and $Y_4$ are independently selected from the group consisting of H and halogen;

$R_1$ is selected from the group consisting of H and C1-C5 alkyl;

$R_2$ is selected from the group consisting of H, C1-C5 alkyl, and C1-C5 alkoxy;

$R_3$ is selected from the group consisting of C1-C10 alkyl and C2-C10 alkenyl; and n is an integral of 1 to 80.

2. The spirocyclic indolone polyethylene glycol carbonate compound, a stereoisomer thereof, or a pharmaceutically acceptable salt thereof according to claim 1, wherein said spirocyclic indolone polyethylene glycol carbonate compound has a structure represented by the following general formula II:

(II)

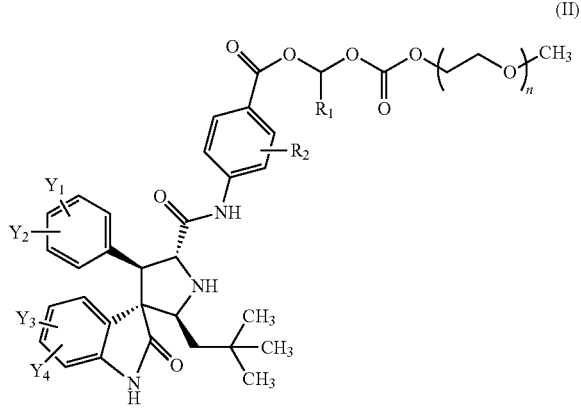

wherein Y$_1$, Y$_2$, Y$_3$, Y$_4$, R$_1$, R$_2$ and n are as defined in claim 1.

3. The spirocyclic indolone polyethylene glycol carbonate compound, a stereoisomer thereof, or a pharmaceutically acceptable salt thereof according to claim 1, wherein Y$_1$, Y$_2$, Y$_3$, and Y$_4$ are independently selected from the group consisting of H, F and Cl.

4. The spirocyclic indolone polyethylene glycol carbonate compound, a stereoisomer thereof, or a pharmaceutically acceptable salt thereof according to claim 1, wherein R$_1$ is selected from the group consisting of H and C1-C3 alkyl; R$_2$ is selected from C1-C5 alkoxy; and R$_3$ is selected from C1-C6 alkyl.

5. The spirocyclic indolone polyethylene glycol carbonate compound, a stereoisomer thereof, or a pharmaceutically acceptable salt thereof according to claim 1, wherein n is an integral of 1 to 60.

6. The spirocyclic indolone polyethylene glycol carbonate compound, a stereoisomer thereof, or a pharmaceutically acceptable salt thereof according to claim 1, wherein said spirocyclic indolone polyethylene glycol carbonate compound is selected from the group consisting of:

rac-9-oxo-2,5,8,10-tetraoxadodecan-11-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate

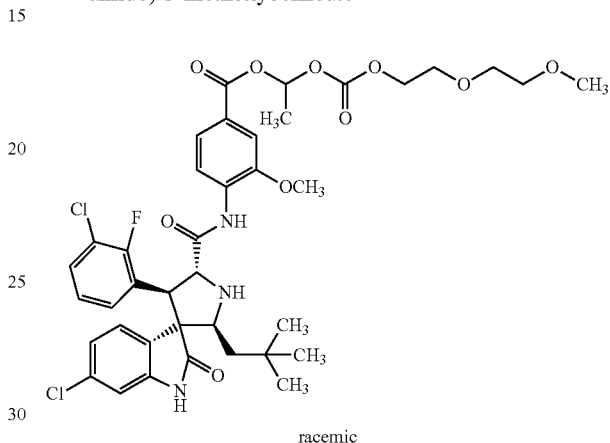

racemic rac-12-oxo-2,5,8,11,13-pentaoxapentadecan-14-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate

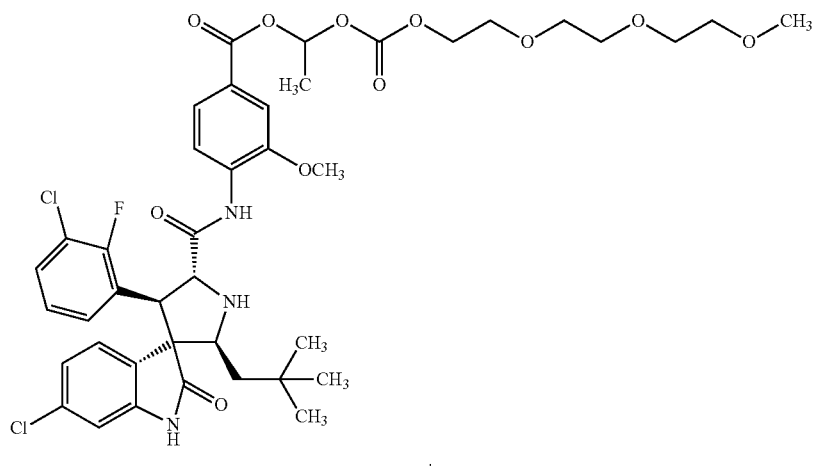

racemic chiral-12-oxo-2,5,8,11,13-pentaoxapentadecan-14-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate

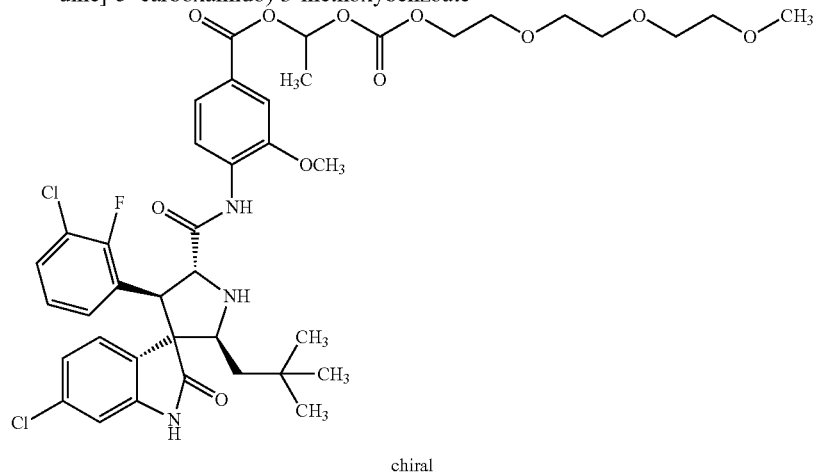

chiral rac-24-oxo-2,5,8,11,14,17,20,23,25-nonoxaheptacosan-26-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate

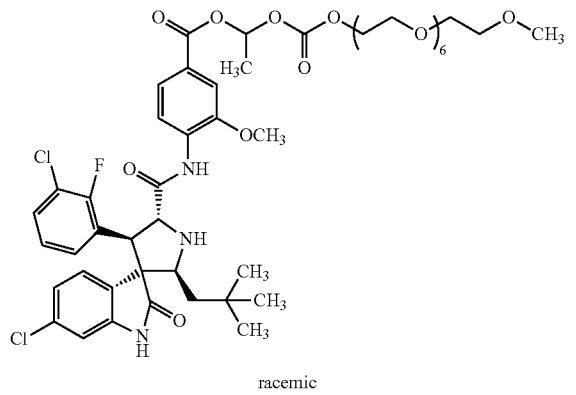

racemic rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid methoxy polyethylene glycol 1000 carbonate

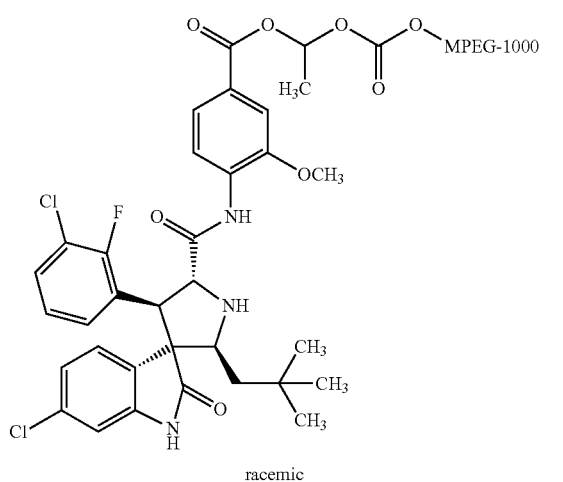

racemic rac-4-((2'S,3'R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoic acid methoxy polyethylene glycol 2000 carbonate

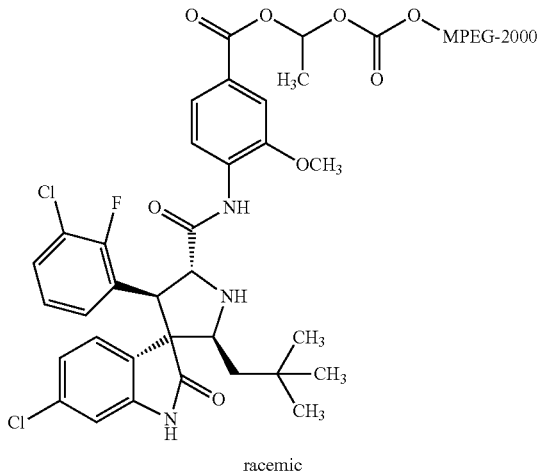

racemic rac-9-oxo-2,5,8,10-tetraoxaundecan-11-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate

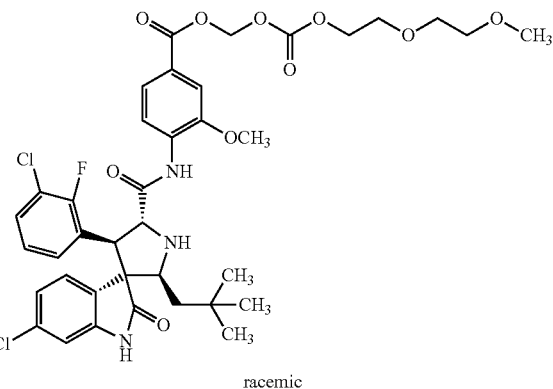

racemic rac-9-oxo-2,5,8,10-tetraoxatridecan-11-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate

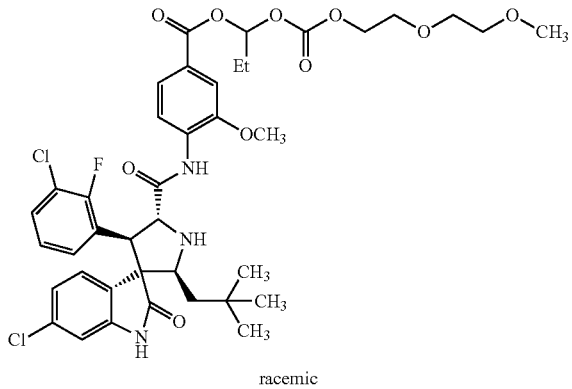

racemic rac-14-methyl-9-oxo-2,5,8,10-tetraoxapentadecan-11-yl-4-((2'S,3R,4'S,5'R)-6-chloro-4'-(3-chloro-2-fluorophenyl)-2'-neopentyl-2-oxospiro[indoline-3,3'-pyrrolidine]-5'-carboxamido)-3-methoxybenzoate

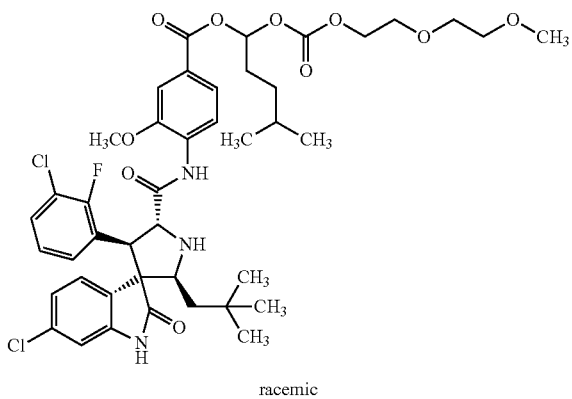

racemic rac-3-oxo-2,4,7,10-tetraoxaundecanyl-4-((2'S,3R,4'S,5'R)-6-chloro-4'-(3-chloro-phenyl)-5-fluoro-2'-neopentyl-2-oxospiro[indoline-3,3'-pyrrolidine]-5'-carboxamido)-3-methoxybenzoate

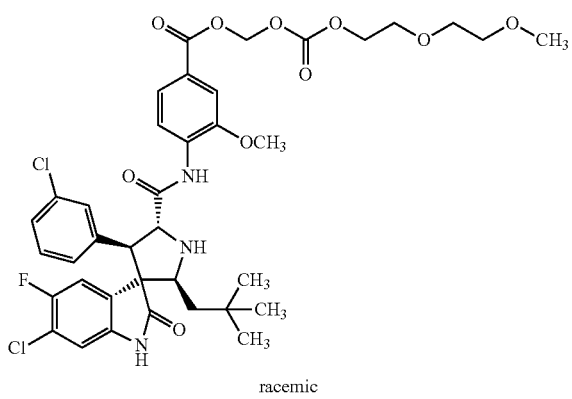

racemic rac-9-oxo-2,5,8,10-tetraoxadodecanyl-4-((2'S,3R,4'S,5'R)-6-chloro-4'-(3-chloro-phenyl)-5-fluoro-2'-neopentyl-2-oxospiro[indoline-3,3'-pyrrolidine]-5'-carboxamido)-3-methoxybenzoate

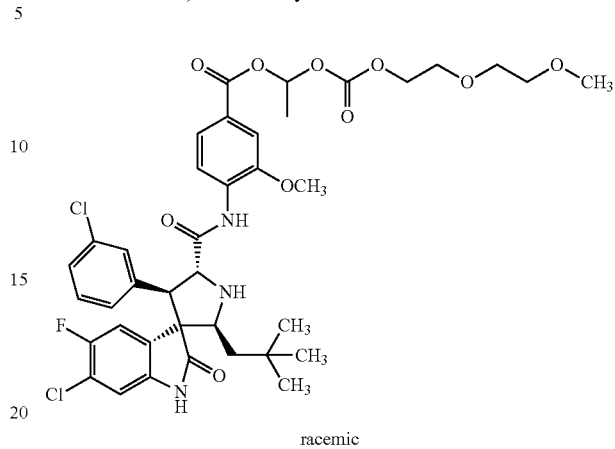

racemic rac-24-oxo-2,5,8,11,14,17,20,23,25-nonoxaheptacosan-26-yl-4-((2'S,3R,4'S,5'R)-6-chloro-4'-(3-chlorophenyl)-2'-neopentyl-2-oxospiro[indoline-3,3'-pyrrolidine]-5'-carboxamido)-3-methoxybenzoate and

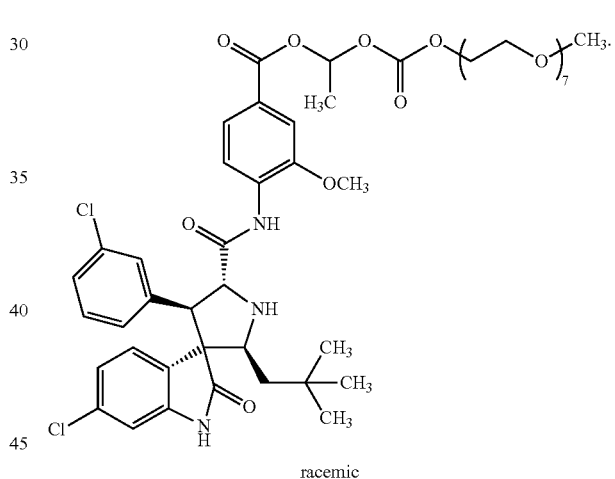

racemic

7. An antitumor pharmaceutical composition, comprising a therapeutically effective amount of a spirocyclic indolone polyethylene glycol carbonate compound, a stereoisomer thereof, or a pharmaceutically acceptable salt thereof as claimed in claim 1, and pharmaceutically acceptable auxiliary material(s).

8. The antitumor pharmaceutical composition according to claim 7, wherein the composition is in a form of an injectable solution, a tablet, or a capsule.

9. A method of treating osteosarcoma comprising administering to an osteosarcoma patient a therapeutically effective amount of a spirocyclic indolone polyethylene glycol carbonate compound, a stereoisomer thereof, or a pharmaceutically acceptable salt thereof as claimed in claim 1.

10. The spirocyclic indolone polyethylene glycol carbonate compound, a stereoisomer thereof, or a pharmaceutically acceptable salt thereof according to claim 1, wherein n is an integral of 2 to 50.

11. The spirocyclic indolone polyethylene glycol carbonate compound, a stereoisomer thereof, or a pharmaceutically acceptable salt thereof according to claim 1, wherein n is an integral of 3 to 50.

* * * * *